United States Patent
Fricker et al.

(10) Patent No.: US 10,716,757 B2
(45) Date of Patent: Jul. 21, 2020

(54) LIPOSOMAL FORMULATION FOR THE ORAL HEPATIC DELIVERY OF DRUGS

(71) Applicant: Universität Heidelberg, Heidelberg (DE)

(72) Inventors: Gert Fricker, Dossenheim (DE); Walter Mier, Bensheim (DE); Frieder Helm, Heidelberg (DE); Philipp Uhl, Heidelberg (DE); Stephan Urban, Neustadt (DE)

(73) Assignee: Universität Heidelberg, Heidelberg (DE)

( * ) Notice: Subject to any disclaimer, the term of this patent is extended or adjusted under 35 U.S.C. 154(b) by 0 days.

(21) Appl. No.: 15/769,596

(22) PCT Filed: Oct. 11, 2016

(86) PCT No.: PCT/EP2016/001680
§ 371 (c)(1),
(2) Date: Apr. 19, 2018

(87) PCT Pub. No.: WO2017/067640
PCT Pub. Date: Apr. 27, 2017

(65) Prior Publication Data
US 2018/0303755 A1   Oct. 25, 2018

(30) Foreign Application Priority Data
Oct. 21, 2015   (EP) ..................................... 15003010

(51) Int. Cl.
*A61K 9/127* (2006.01)
*A61K 47/10* (2017.01)
(Continued)

(52) U.S. Cl.
CPC ............ *A61K 9/1272* (2013.01); *A61K 47/10* (2013.01); *A61K 47/26* (2013.01); *A61K 51/08* (2013.01);
(Continued)

(58) Field of Classification Search
CPC ...... A61K 9/127; A61K 9/1272; A61K 51/08; A61K 51/1234; A61K 47/10; A61K 47/26; A61K 2123/00; A61P 1/16; A61P 31/20
See application file for complete search history.

(56) References Cited

U.S. PATENT DOCUMENTS

| | | | |
|---|---|---|---|
| 6,403,117 B1 * | 6/2002 | Sprott | A61K 9/1272 424/1.21 |
| 2012/0039988 A1 * | 2/2012 | Wu | C07K 7/08 424/450 |
| 2013/0251783 A1 | 9/2013 | Parmentier | |

FOREIGN PATENT DOCUMENTS

CN           101744768           *  6/2010

OTHER PUBLICATIONS

Zhang et al., Hepatitis B virus preS1-derived lipopeptide functionalized liposomes for targeting hepatic cells, 2014, Biomaterials vol. 23, pp. 6130-6141.
Parmentier et al., Oral peptide delivery by tetraether lipid liposomes, 2011, Intl J Pharmaceutics vol. 415, pp. 150-157.
(Continued)

*Primary Examiner* — Gollamudi S Kishore
(74) *Attorney, Agent, or Firm* — HelixIP LLP

(57) ABSTRACT

The present invention relates to liposomal compositions, comprising liposomes containing tetraether lipids (TELs), and further comprising the lipopeptide Myr-HBVpreS/2-48 (Myrcludex B) as part of said liposomes, as well as uses thereof for the prevention or treatment of hepatic disorders
(Continued)

or diseases, and/or for the oral hepatic delivery of therapeutic and/or diagnostic agents.

2 Claims, 24 Drawing Sheets

Specification includes a Sequence Listing.

(51) Int. Cl.
    *A61K 47/26*     (2006.01)
    *A61K 51/08*     (2006.01)
    *A61K 51/12*     (2006.01)
    *A61P 1/16*     (2006.01)
    *A61P 31/20*     (2006.01)

(52) U.S. Cl.
    CPC ............ *A61K 51/1234* (2013.01); *A61P 1/16* (2018.01); *A61P 31/20* (2018.01); *A61K 2123/00* (2013.01)

(56) References Cited

OTHER PUBLICATIONS

Qin et al, Liposome formulated with Tat-modified cholesterol for improving brain delivery and therapeutic efficacy on . . . , 2011, Int J Pharmaceut vol. 420, pp. 304-312.

Sawant et al., Therapeutic delivery using cell-penetrating peptides CPPs: Tools for crossing the cell membrane and molecular mechanism, 2013, Eur J Nanomed vol. 5, pp. 141-158.

\* cited by examiner

SEQUENCE LISTING

```
<160> NUMBER OF SEQ ID NOS: 1

<210> SEQ ID NO 1
<211> LENGTH: 47
<212> TYPE: PRT
<213> ORGANISM: Hepatitis B virus

<400> SEQUENCE: 1

Gly Gln Asn Leu Ser Thr Ser Asn Pro Leu Gly Phe Phe Pro Asp His
1               5                   10                  15

Gln Leu Asp Pro Ala Phe Arg Ala Asn Thr Ala Asn Pro Asp Trp Asp
```

-continued

```
                20              25              30
Phe Asn Pro Asn Lys Asp Thr Trp Pro Asp Ala Asn Lys Val Gly
        35                  40                  45
```

LIPOSOMAL FORMULATION FOR THE ORAL HEPATIC DELIVERY OF DRUGS The present invention relates to liposomal compositions, comprising liposomes containing tetraether lipids (TELs), and further comprising the lipopeptide Myr-HBVpreS/2-48 (Myrcludex B) as part of said liposomes, as well as uses thereof for the prevention or treatment of hepatic disorders or diseases, and/or for the oral hepatic delivery of therapeutic and/or diagnostic agents.

Oral drug delivery is considered as the most advantageous way of application, in particular for the treatment of chronic diseases, which demand long-term and repeated drug administration. The oral route offers high drug safety and is widely accepted among patients due to its convenience. Additionally, non-sterility of oral drug forms reduces costs in production, storage and distribution, which could contribute to health care improvement in third world countries. It is estimated, that 90% of all marketed drug formulations are for oral use.

Figure 1:
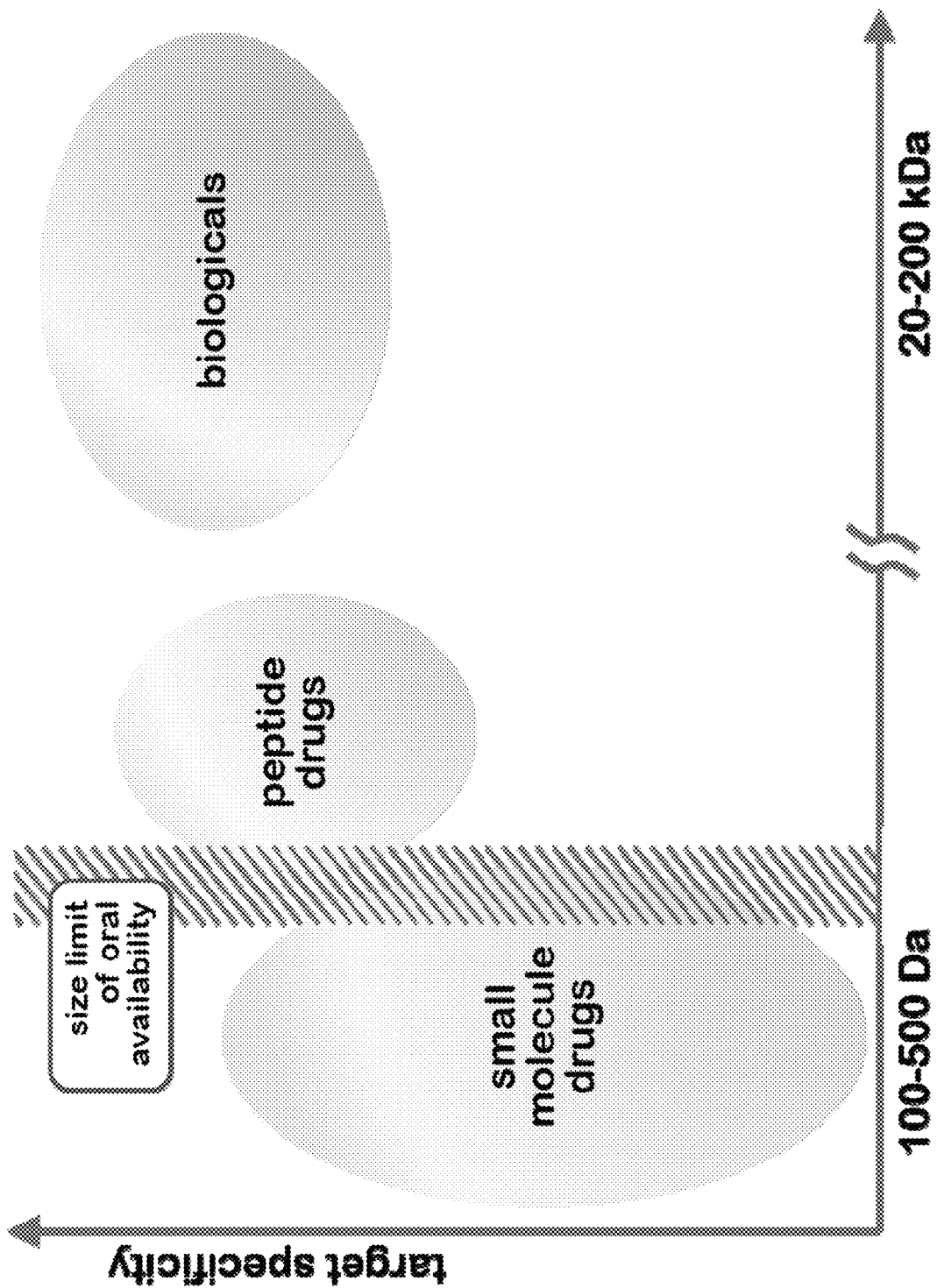
Figure 2:
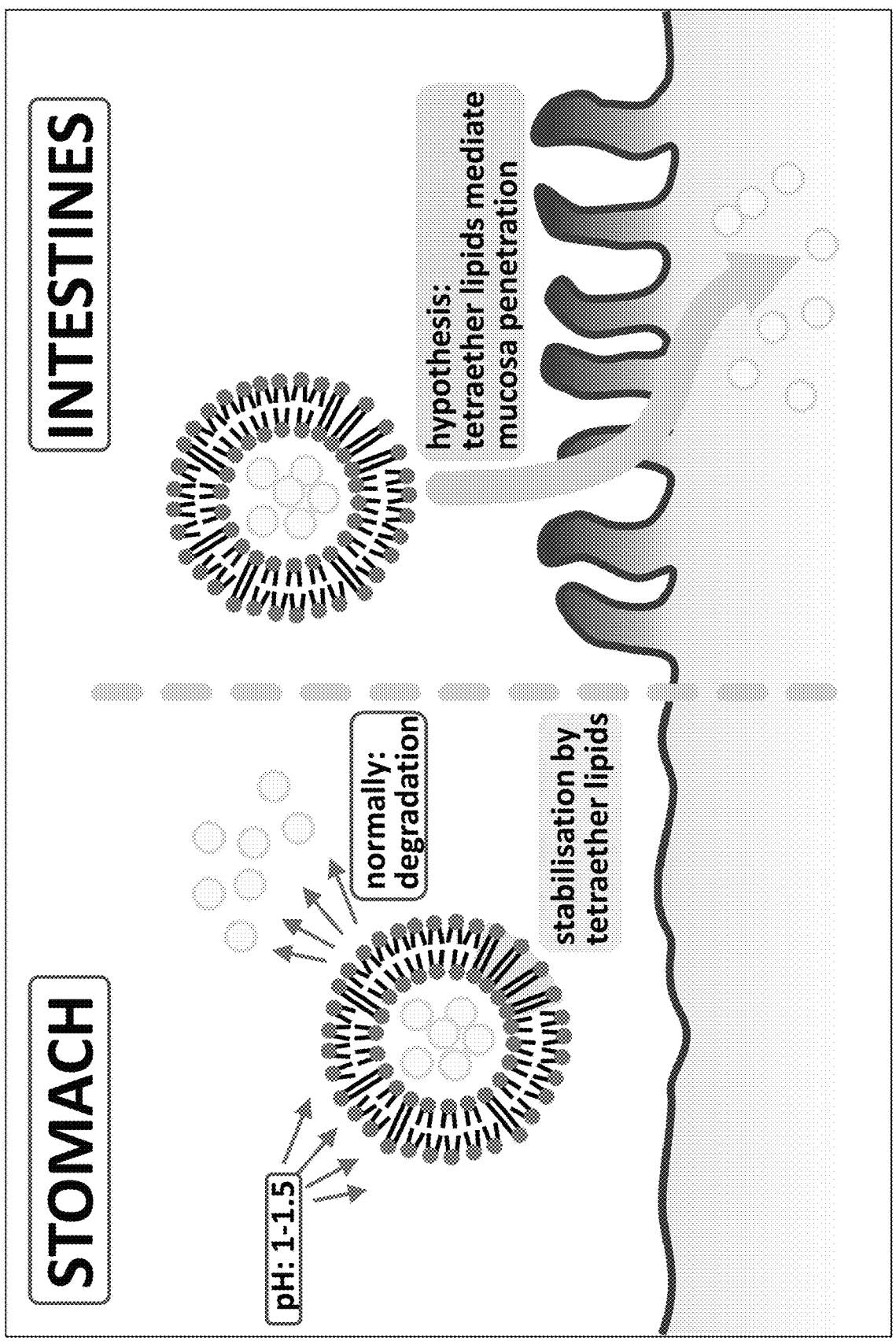

However, many drugs, particularly peptides and other macromolecular drugs, show both a very poor stability under the acid conditions in the stomach after oral administration and also poor absorption across the gastrointestinal barrier (FIGS. 1 and 2). To overcome this problem, different approaches to improve the bioavailability have been tested in the past years including solid lipid nanoparticles, nano- or micro-emulsions, or liposomes. However, conventional liposomal formulations have not been very convincing due to their instability in the gastrointestinal tract (GIT).

A significant improvement in liposomes can be made by the combination of conventional phospholipids (PLs) and so-called tetraether lipids (TELs) (FIG. 3), specific lipids derived from archaea, e.g. the extremophilic archaeon *Sulfolobus acidocaldarius*. Recent studies showed that these TELs can both improve the liposomal stability in the GIT and also mediate mucosal penetration.

*S. acidocaldarius* grows at temperatures between 50 to 100° C. mostly under acidic conditions, making a stable cell membrane inevitable. Archaeal membrane lipids comprise mainly $C_{20}$-$C_{40}$ isoprenoid-subunit backbones, linked by ether bonds to glycerol and/or nonitol bridge group(s). The bridge group is either unsubstituted or substituted with one of a wide variety of polar or nonpolar head groups. The quantity of these moieties in the archaeal cell membrane differs with growth conditions and increases with the environmental temperature. The TELs glycerylcaldityltetraether (GCTE) and diglyceryltetraether (DGTE) with an average number of four to six cyclopentyl rings can be isolated from *S. acidocaldarius*.

Liver diseases, such as viral hepatitis, autoimmune hepatitis, hereditary hemochromatosis, non-alcoholic fatty liver disease (NAFLD) and Wilson's disease, are associated with an increased risk for the development of liver cirrhosis and hepatocellular carcinoma. Additional risk factors are toxins, like alcohol and aflatoxin. While the prevalence of autoimmune hepatitis and metabolic disorders, like hemochromatosis and Wilson's disease, is vanishingly low, more than 500 million people worldwide are persistently infected with the hepatitis B and/or hepatitis C virus. Up to one million people die due to hepatitis B (HBV) infections and their consequences, annually. As the disease is only associated with nonspecific symptoms (the most common ones being malaise and fatigue), the risk of developing liver cirrhosis or hepatocellular carcinoma is increased. An estimated 57% of the total hepatic cirrhosis and 78% of the primary hepatocellular carcinomas are the result of hepatitis B/hepatitis C (HCV) infections. Acute HBV infection is treated symptomatically and, unfortunately, chronic HBV infection is not curable. This highlights the importance for hepatitis infections to be diagnosed at an early stage to enable an optimal treatment.

In view of the above, the technical problem underlying the present invention is the provision of means for the hepatic delivery of drugs via the oral route.

The solution to the above technical problem is achieved by the embodiments characterized in the claims.

In particular, in a first aspect, the present invention relates to a liposomal composition comprising:
(a) liposomes comprising tetraether lipids (TELs), and
(b) the lipopeptide Myr-HBVpreS/2-48 (Myrcludex B) as part of said liposomes.

As used herein, the term "liposomal composition" relates to a composition comprising liposomes. The term "liposome" as used herein refers to artificially prepared vesicles composed of lipid bilayers. Liposomes can be used for delivery of agents due to their unique property of encapsulating a region of aqueous solution inside a hydrophobic membrane. Dissolved hydrophilic solutes cannot readily pass through the lipid bilayer. Hydrophobic compounds can be dissolved in the lipid bilayer, and in this way liposomes can carry both hydrophobic and hydrophilic compounds. To deliver the molecules to sites of action, the lipid bilayer can fuse with other bilayers such as cell membranes, thus delivering the liposome contents. By making liposomes in a solution of an agent, it can be delivered to the inner lumen of the liposome.

TELs that can be used for the formation of liposomes are not particularly limited and are known in the art. In particular embodiments, said TELs are derived from an archaeal species of the genus *Sulfolobus*, e.g. *S. islandicus* or *S. acidocaldarius*, wherein the latter is particularly preferred. In a preferred embodiment, the TELs are selected from the group consisting of glycerylcaldityltetraether (GCTE), diglyceryltetraether (DGTE), and combinations thereof.

Preferably, the liposomes used in the compositions of the present invention comprise said TELs in an amount of above 0 mol-% to 25 mol-%, preferably 1 to 25 mol-%, more preferably 1 to 10 mol-%, more preferably 3 to 7 mol-%, more preferably 4 to 6 mol-% based on the total lipid amount. In specific embodiments, said liposomes comprise said TELs in an amount of about 5 mol-% based on the total lipid amount.

Besides the presence of TELs as described above, the liposomes used in the compositions according to the present invention are not particularly limited to specific lipids. In particular, the lipids used for the generation of said liposomes can be any suitable lipids known in the art. These lipids include—but are not restricted to—cholesterol or derivatives thereof, phospholipids, lysophospholipids or further tetraetherlipids. Accordingly, in a preferred embodiment, said liposomes comprise one or more lipids, selected from the group consisting of cholesterol and derivatives thereof, phospholipids, lysophospholipids, and tetraetherlipids. Preferably, said liposomes comprise phospholipids, wherein said phospholipids can be synthetic, semi-synthetic or natural phospholipids. In general, suitable lipids can be selected from the group consisting of phosphatidylcholines, phosphatidylethanolamines, phosphatidylinosites, phosphatidylserines, cephalines, phosphatidylglycerols, and lysophospholipids. In a particular embodiment of the present invention, the liposomes comprise egg phosphatidylcholine (E-PC; lecithin) and cholesterol, preferably in an amount of about 80 to 90 mol-%, preferably about 85 mol-% E-PC and about 5 to 15 mol-%, preferably about 10 mol-% cholesterol. The liposomes to be used according to the present invention may further comprise any further suitable agents such as e.g. enzyme inhibitors, permeation enhancers, or other lipophilic or hydrophilic substances that can be used for the stabilization of liposomes or for altering liposome properties. Such lipophilic or hydrophilic substances are not particularly limited and are known in the art. They include for example vitamin E, fatty acids, waxes, and mono-, di- and triglycerides. Furthermore, substances that enhance the bioavailability of enclosed active agents, like enzyme inhibitors, tight junction modulators or chelating agents can be added.

The lipids used for preparation of these liposomes can also be attached to target seeking structures such as peptide sequences, antibodies, receptor ligands and surfactants.

In a preferred embodiment, the liposomes comprised in the composition of the present invention exhibit a Z-Average measured by dynamic light scattering after dilution in aqueous medium of at most 350 nm and a polydispersity index (PDI) of at most 0.3, where a Z-Average of 100 to 250 nm and a polydispersity index of at most 0.2 is particularly preferred.

Methods for the generation of liposomes are not particularly limited and are known in the art. They include for example high pressure homogenization, extrusion and dual asymmetric centrifugation (DAC).

According to the present invention, the above liposomal compositions comprise the lipopeptide Myr-HBVpreS/2-48 (Myrcludex B) as part of the liposomes. In this context, the term "comprise the lipopeptide as part of the liposomes" as used herein relates to the fact that said lipopeptide is present in the inner lumen of the liposomes and/or is incorporated into the liposomal lipid bilayer. In this context, Myrcludex B can be incorporated into the lipid bilayer via its fatty acid chain.

Myrcludex B is linear peptide consisting of 47 amino acids corresponding to amino acids 2 to 48 of the hepatitis B virus (HBV) preS protein (SEQ ID NO: 1; GQNLSTSN-PLGFFPDHQLDPAFRANTANPDWDFNPNKDTWP-DANKVG) with a myristoylation on the N-terminus, having a molecular weight of 5366 g/mol. It is an investigational drug for hepatitis B treatment. However, as a macromolecular drug, Myrcludex B per se shows only poor oral bioavailability (<1%), so that only subcutaneous application is so far possible resulting in low patient compliance and high medical costs. However, when used in the liposomal compositions of the present invention, the oral bioavailability and hepatic delivery of Myrcludex B can be significantly increased. Therefore, the liposomal compositions of the present invention can be for use in the prevention and/or treatment of hepatitis B.

Moreover, in the present invention, Myrcludex B has been identified as showing pronounced hepatotropism, i.e., a high selective accumulation in liver tissue. Therefore, the liposomal compositions of the present invention can be used as an orally administered drug delivery system exhibiting a high hepatic targeting efficacy.

In accordance with this aspect of the present invention, the liposomal compositions of the present invention can further comprise at least one additional therapeutic agent and/or at least one diagnostic agent.

Respective therapeutic agents are not particularly limited and include any agents for which a targeted oral delivery to the liver might be relevant. In preferred embodiments, the above at least one additional therapeutic agent is selected from the group consisting of protein kinase inhibitors, e.g. sorafenib, cytostatic agents, e.g. cisplatin or doxorubicin, and antibiotics.

Further, respective diagnostic agents are not particularly limited and include any agents for which a targeted oral delivery to the liver might be relevant. In preferred embodiments, the above at least one diagnostic agent is selected from the group consisting of agents for the diagnosis of hepatocellular carcinoma (HCC).

The above agents may be present in the liposomal compositions of the present invention enclosed in the liposomes, i.e., in the inner lumen of said liposomes, e.g. when said agents are hydrophilic, or integrated into the liposomal membrane, e.g. when said agents are lipophilic. Further, said agents may not be associated with Myrcludex B, or may be associated with Myrcludex B by non-covalent interactions, or may be covalently bonded to Myrcludex B. In this context, the encapsulation of therapeutic and/or diagnostic agents depends on the hydrophilicity of said agents and the liposome preparation method.

In a preferred embodiment, the content of therapeutic and/or diagnostic agent in the liposomal compositions according to the present invention is above 0 mol-% and at most 50 mol-% in regard to the used amount of agent.

In accordance with the above aspect, the liposomal compositions of the present invention can be for use in the prevention and/or treatment of a hepatic disorder or disease in a subject.

Hepatic disorders and diseases that can be treated in this respect are not particularly limited and are known in the art. They include preferably hepatic disorders or diseases that are selected from the group consisting of viral hepatitis, autoimmune hepatitis, hereditary hemochromatosis, non-alcoholic fatty liver disease (NAFLD), Wilson's disease, liver cirrhosis, and hepatocellular carcinoma.

Preferably, the liposomal compositions for use of the present invention are for oral administration.

Recent studies showed that pretreatment with the proton pump inhibitor omeprazole decreases the diffusion of protons into liposomes and, as a consequence, decreases the denaturation of the encapsulated agents such as proteins by raising the pH in the stomach.

Accordingly, in a preferred embodiment of the liposomal compositions for use according to the present invention, the subject is pretreated with a proton pump inhibitor, wherein said proton pump inhibitor is preferably omeprazole (6-methoxy-2-[(4-methoxy-3,5-dimethylpyridin-2-yl)methanesulfinyl]-1H-1,3-benzodiazole), pantoprazole ((RS)-6-(difluoromethoxy)-2-[(3,4-dimethoxypyridin-2-yl)methylsulfinyl]-1H-benzo[d]imidazole), esomeprazole ((S)-5-methoxy-2-[(4-methoxy-3,5-dimethylpyridin-2-yl)methylsulfinyl]-3H-benzoimidazole), lansoprazole ((RS)-2-([3-methyl-4-(2,2,2-trifluoroethoxy)pyridin-2-yl]methylsulfinyl)-1H-benzo[d]imidazole), and/or rabeprazole ((RS)-2-([4-(3-methoxypropoxy)-3-methylpyridin-2-yl]methylsulfinyl)-1H-benzo[d]imidazole).

Advantageously, the liposomal compositions of the present invention can be freeze-dried, e.g. using 300 to 500 mM sucrose as a lyoprotector, which enables the long-term storage of said compositions.

In a related second aspect, the present invention relates to the use of a liposomal composition of the present invention for the oral hepatic delivery of at least one therapeutic agent and/or at least one diagnostic agent.

In this context, the term "oral hepatic delivery" relates to the delivery of one or more agents to liver tissue by way of oral administration of said agents.

In this aspect, all relevant limitations and definitions provided for the first aspect of the present invention apply in an analogous manner. In particular, the liposomal compositions, therapeutic agents, and diagnostic agents are as defined above.

In a further related aspect, the present invention relates to a method of preventing or treating a hepatic disorder or disease in a subject, comprising the step of administering, preferably orally administering, a liposomal composition of the present invention to said subject.

In yet a further related aspect, the present invention relates to a method of delivering at least one therapeutic agent and/or at least one diagnostic agent to the liver of a subject, comprising the step of administering, preferably orally administering, a liposomal composition of the present invention to said subject.

In these two aspects, all relevant limitations and definitions provided for the first aspect of the present invention apply in an analogous manner. In particular, the liposomal compositions, therapeutic agents, diagnostic agents, and hepatic disorders or diseases are as defined above.

As used herein, the term "about" is intended to be a modifier of ±10% of the specified value. As an example, the term "about 5%" is intended to encompass the range of 4.5 to 5.5%.

The terms "comprising/comprises", "consisting of/consists of", and "consisting essentially of/consists essentially of" are used herein in an interchangeable manner, i.e., each of said terms can expressly be exchanged against one of the other two terms.

The figures show:

FIG. 1:
Peptide drugs and other biologicals show poor oral availability with increasing size.

FIG. 2:
Degradation in the stomach and poor mucosa penetration are the main hurdles that prevent the oral availability of biologicals. Using TEL-liposomes, both hurdles can be overcome.

Figure 3:
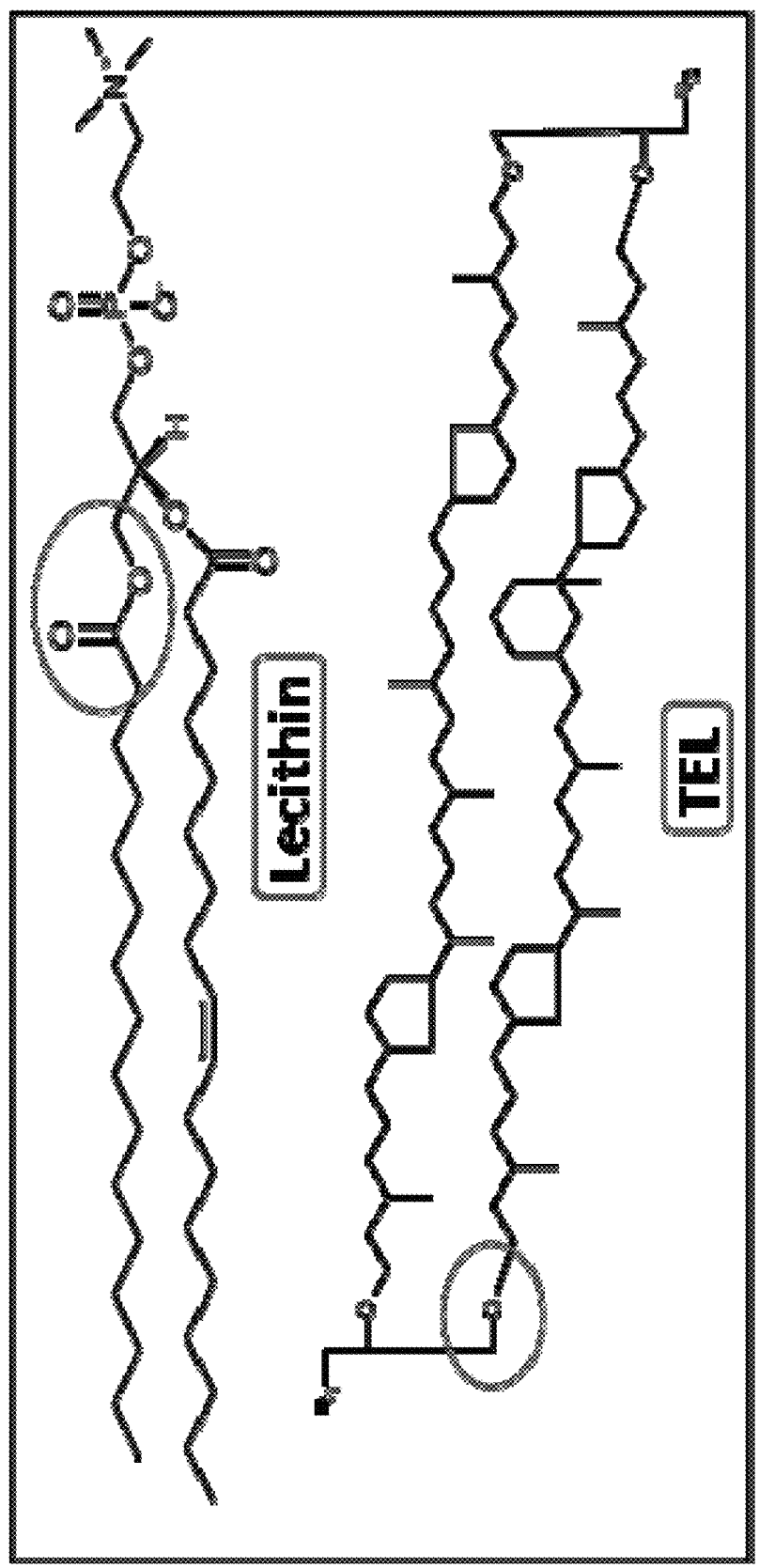

FIG. 3:
Comparison of standard lipids (lecithin; ester bonds) and TELs (ether bonds).

Figure 4:
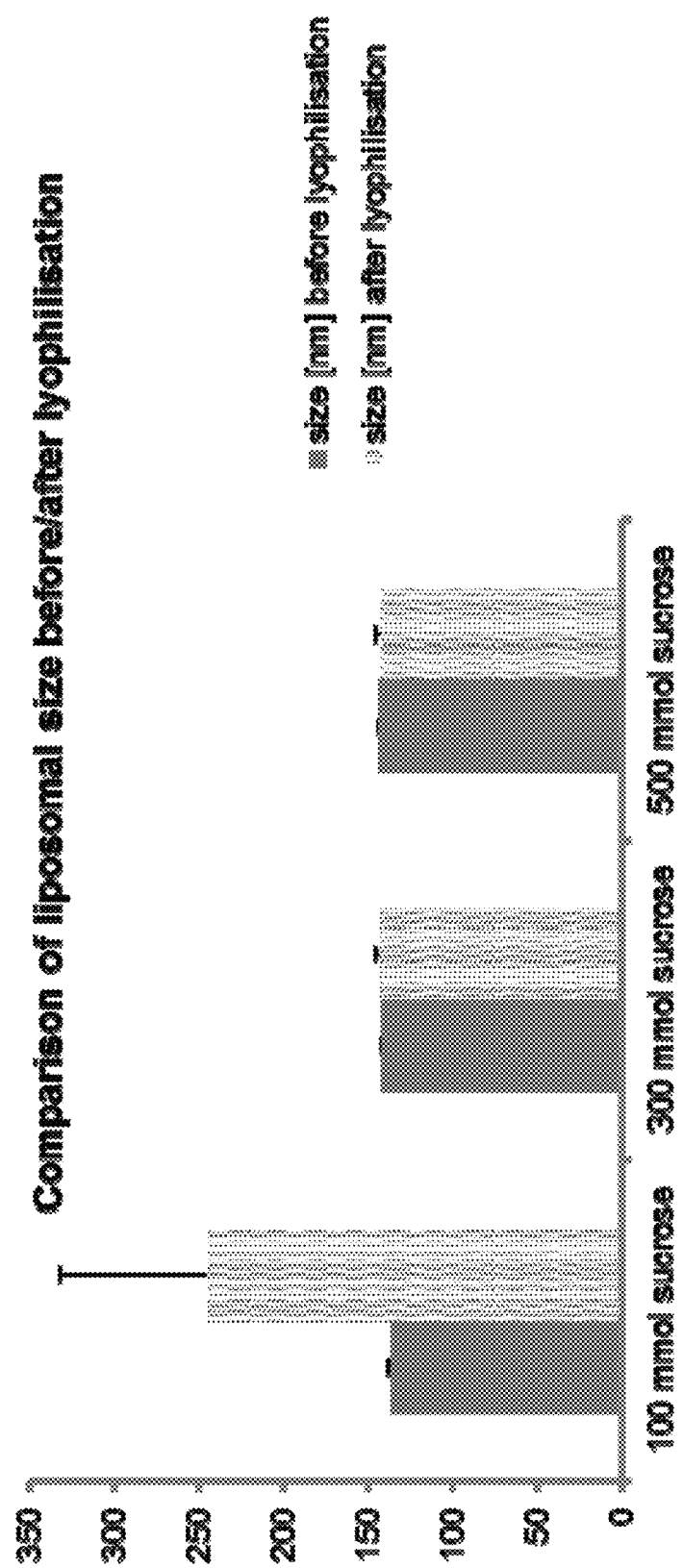
Figure 4:
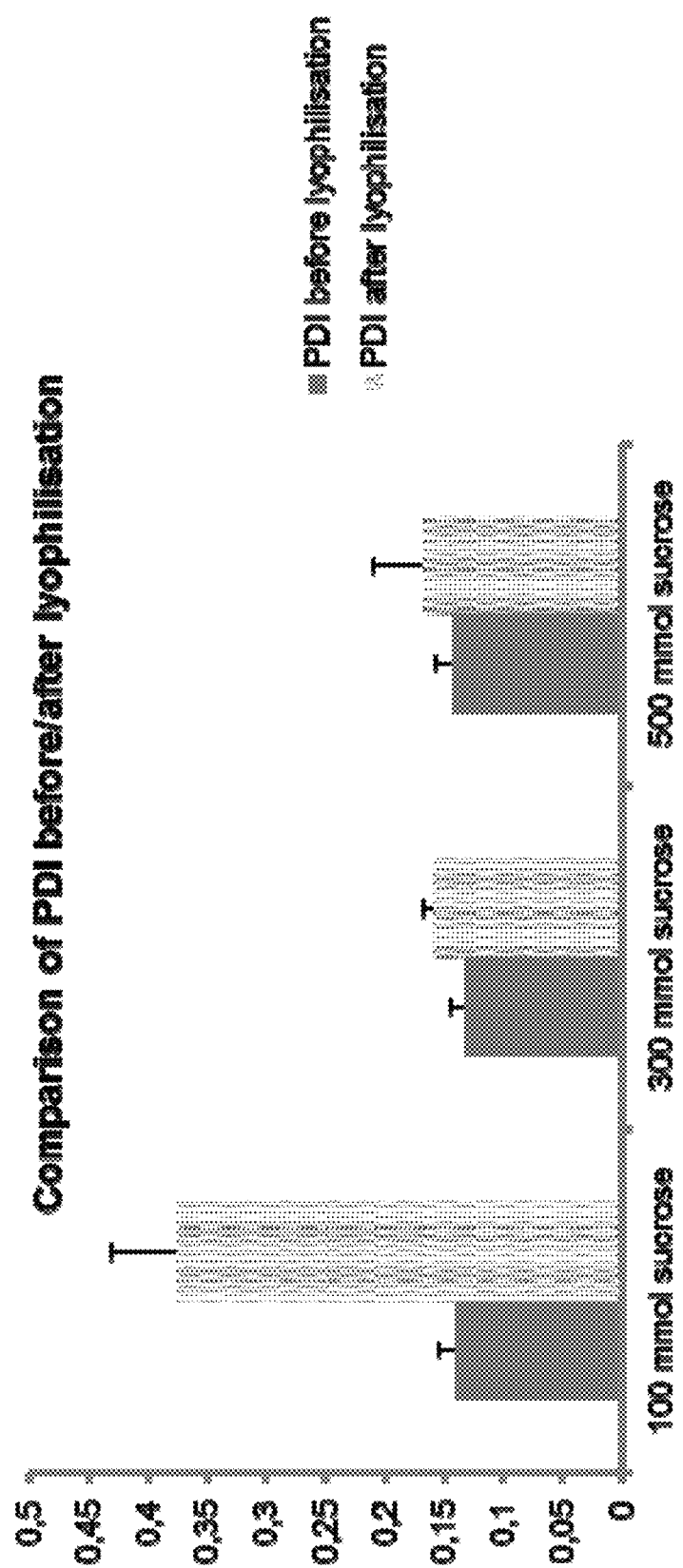

FIG. 4:
Comparison of the liposomal size (A) and the PDI (B) before/after lyophilisation using 100-500 mmol sucrose as lyoprotector. For this formulation the lowest possible concentration of sucrose is 300 mmol.

Figure 5:
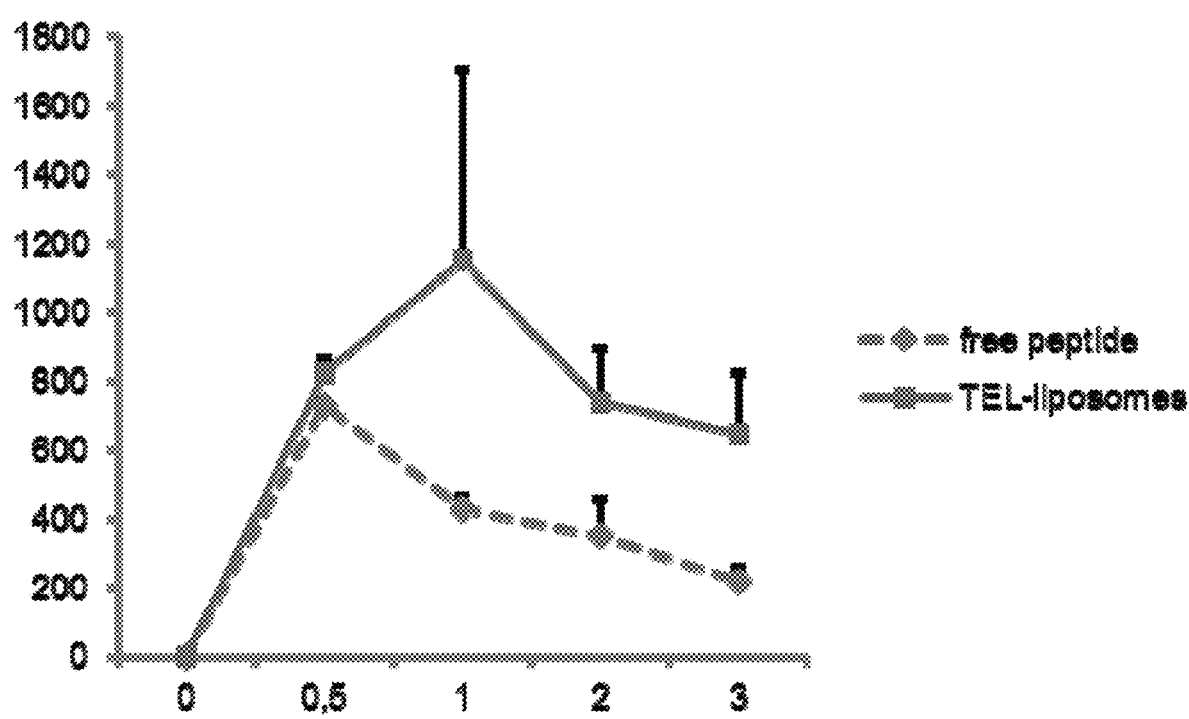

FIG. 5:
Determined blood levels of the control group (dashed line) and the TEL-liposomes group (full line).

Figure 6:
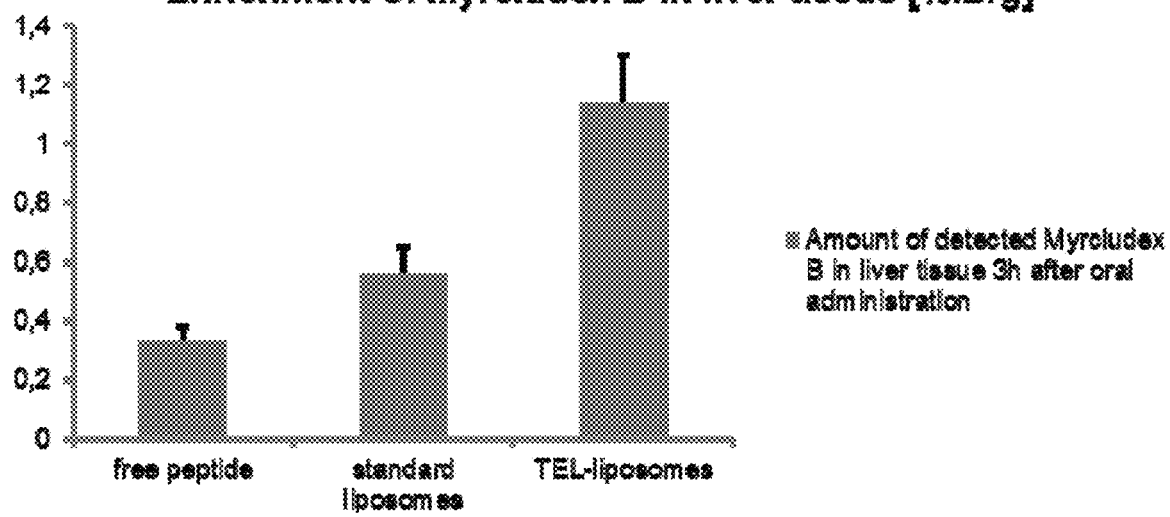
Figure 6:
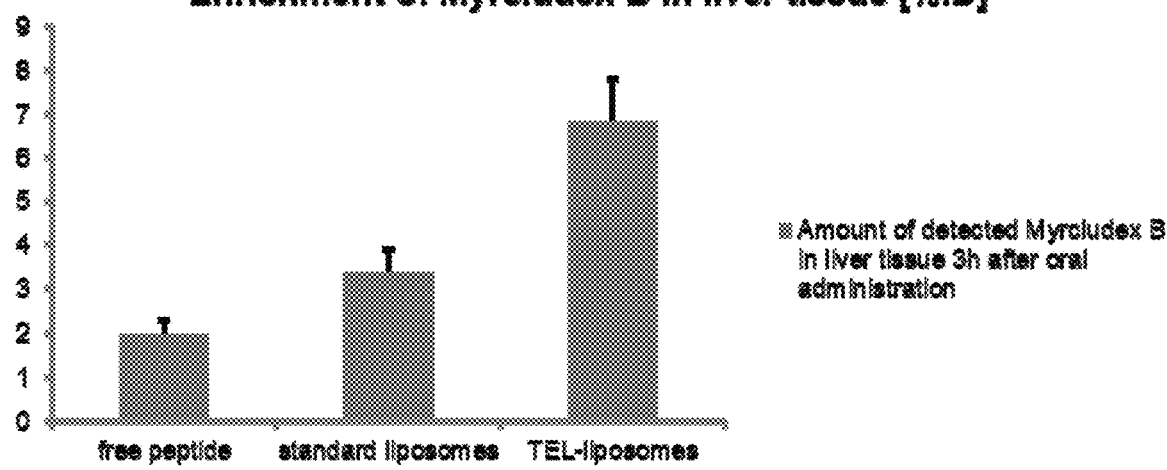

FIG. 6:
Enrichment of different formulations of Myrcludex B in liver tissue [% ID/g] and [%/ID] after oral administration.

Figure 7:
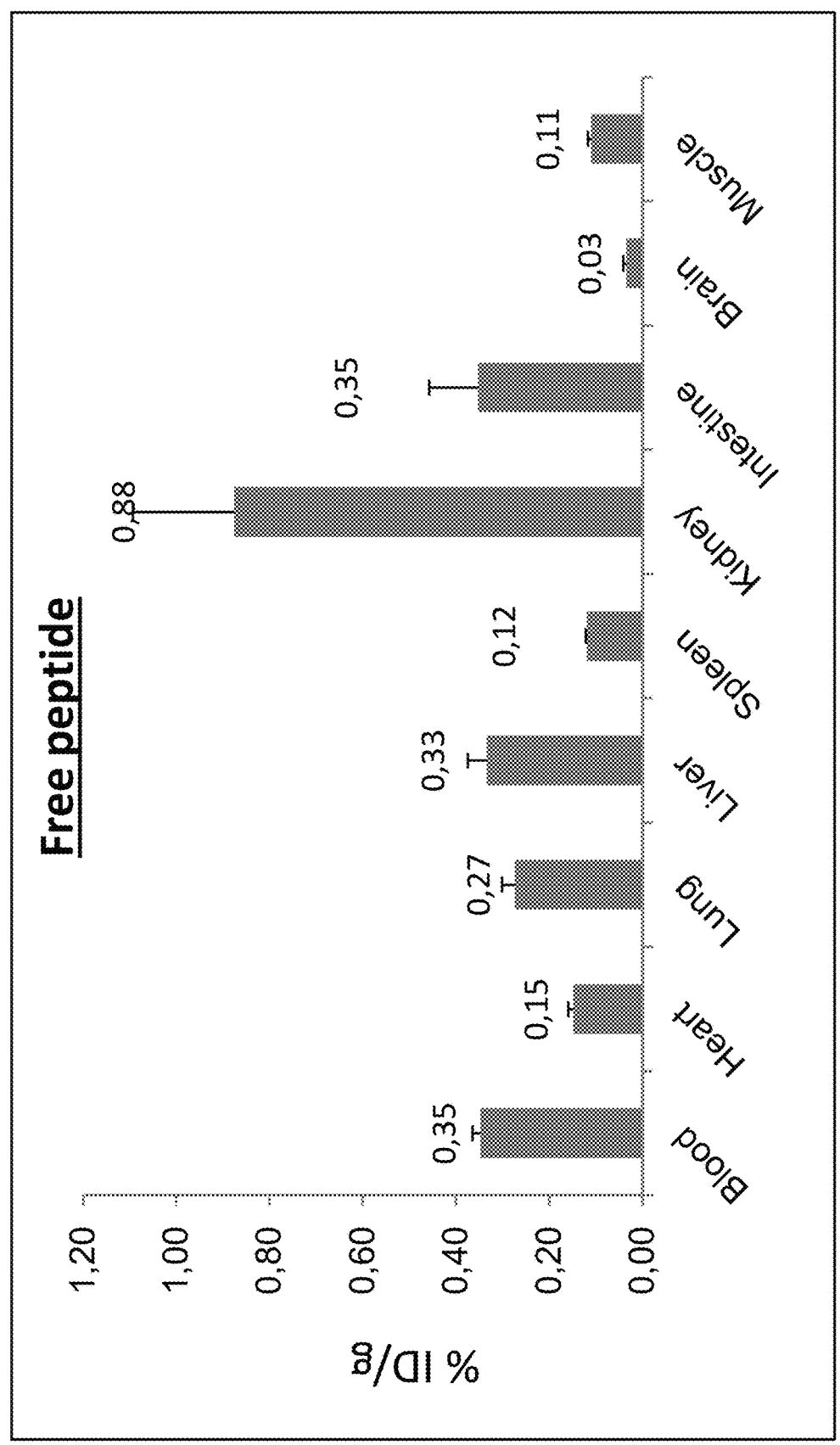

FIG. 7:
Distribution of Myrcludex B in Wistar rats after 5 h; injected dose: 500 µl of the labeled free peptide.

Figure 8:
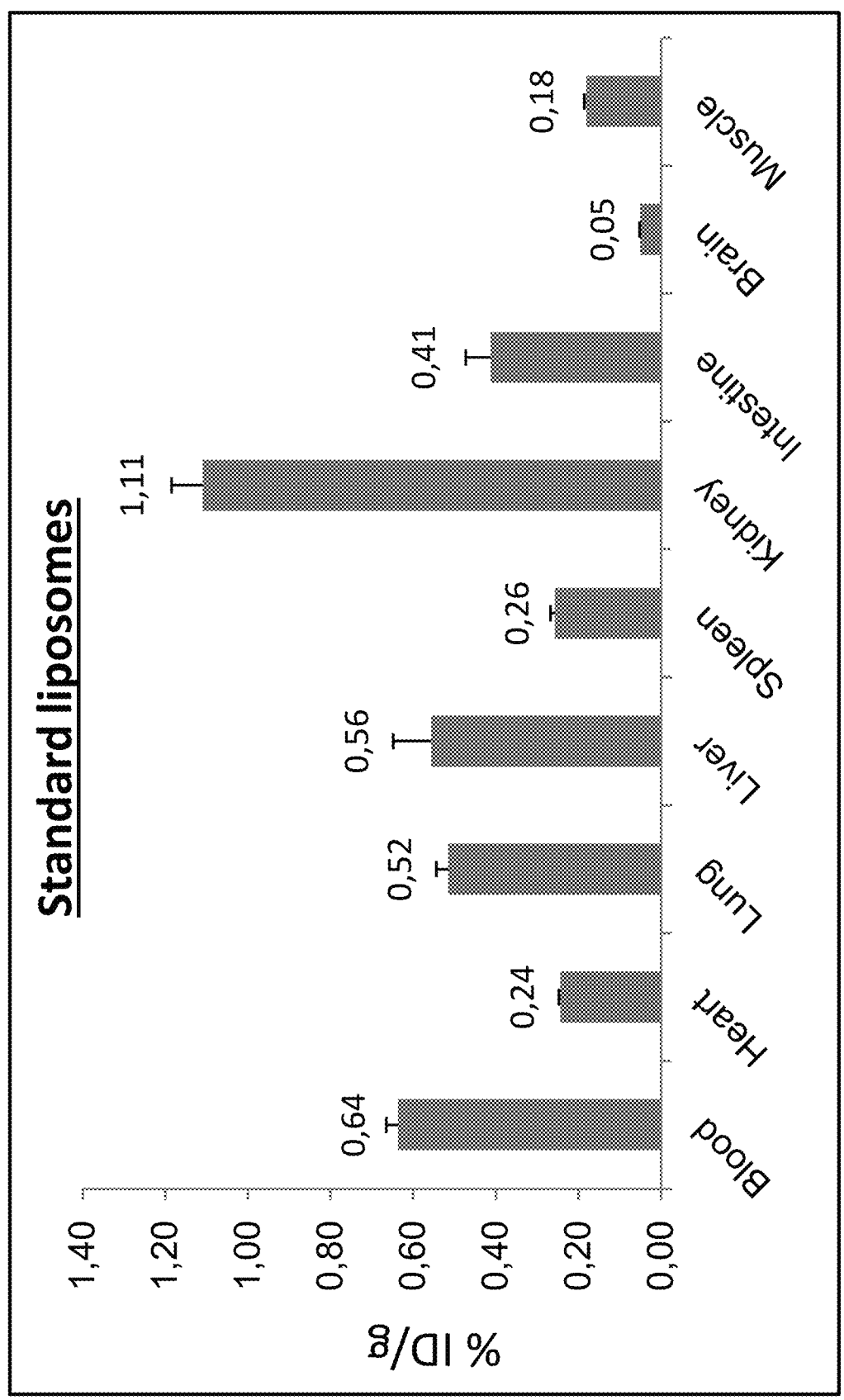

FIG. 8:
Distribution of Myrcludex B in Wistar rats after 5 h; injected dose: 500 µl of the standard liposomal formulation.

Figure 9:
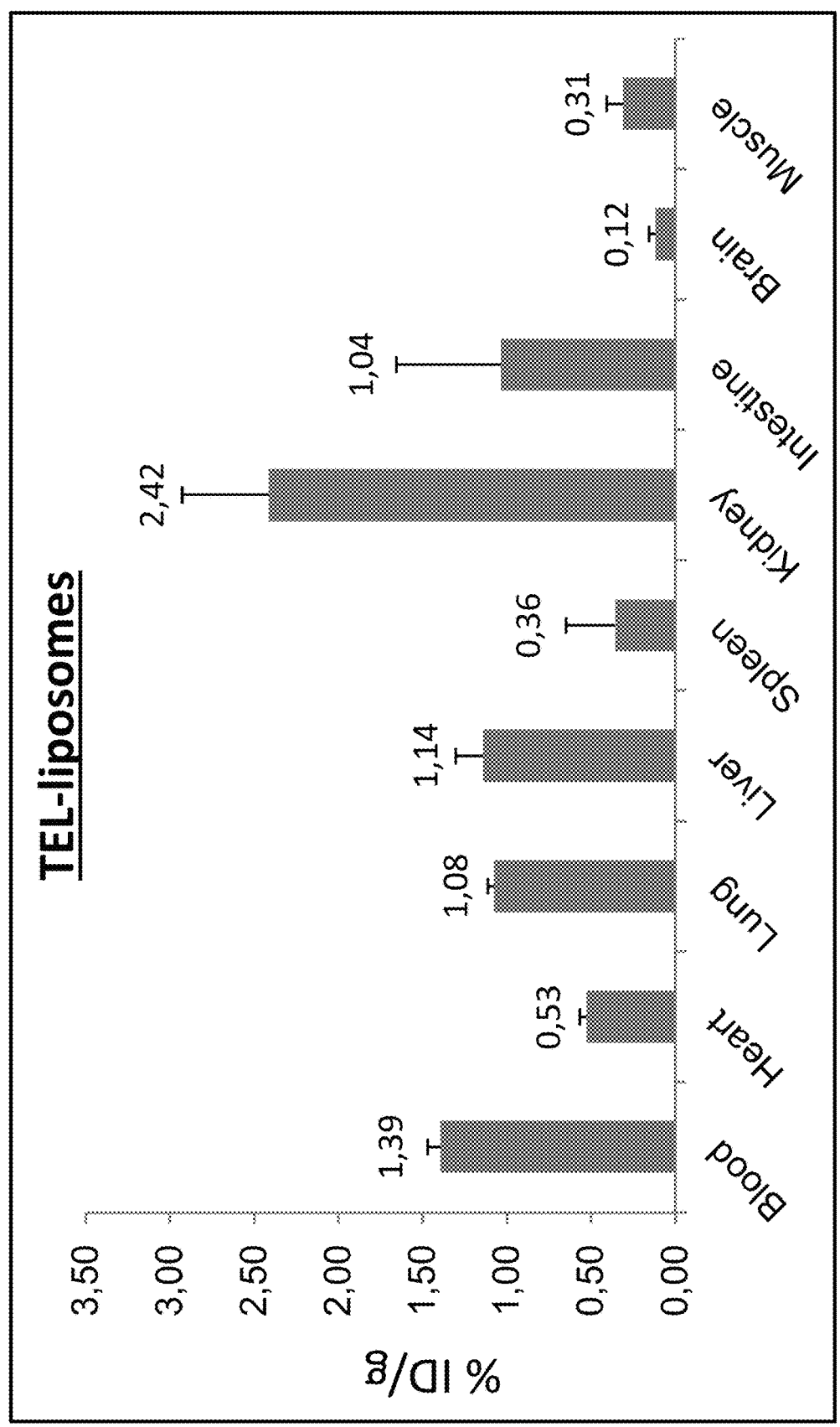

FIG. 9:
Distribution of Myrcludex B in Wistar rats after 5 h; injected dose: 500 µl of the TEL-liposomal formulation.

Figure 10:
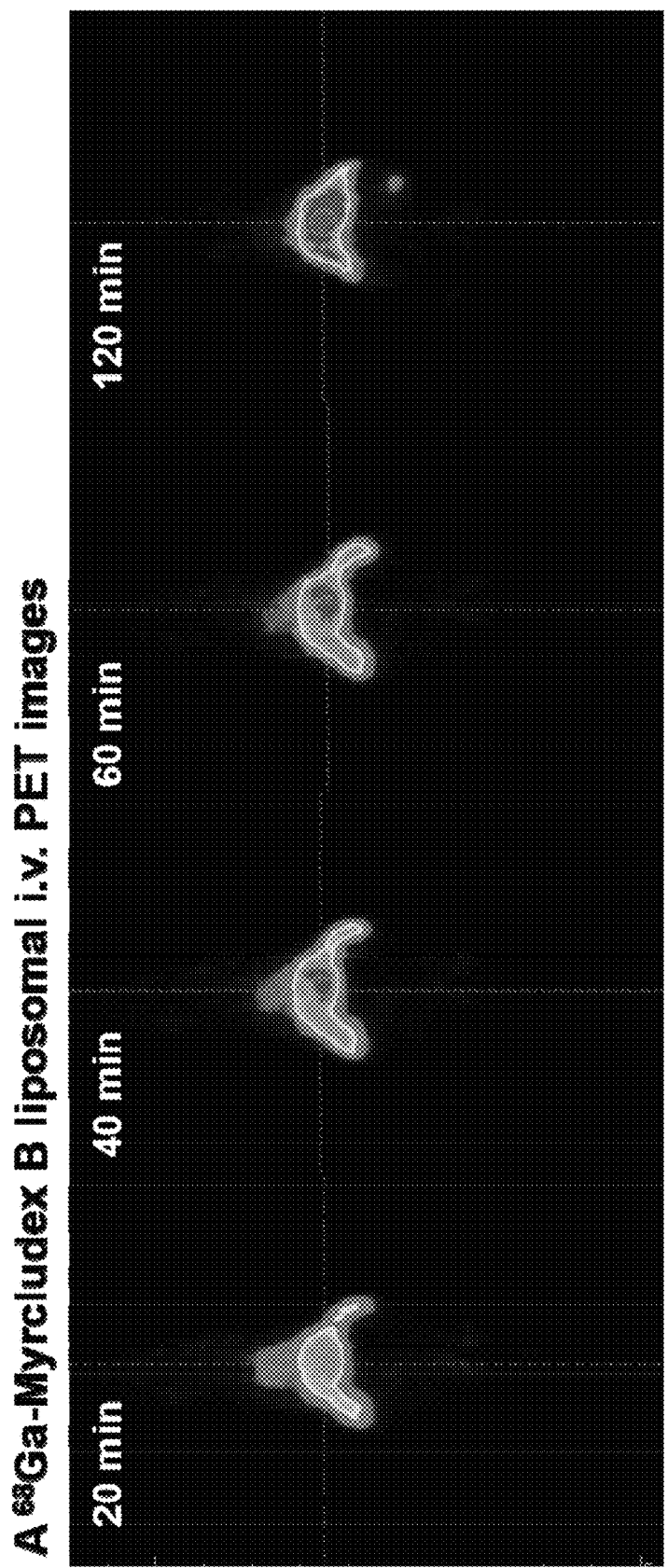
Figure 10:
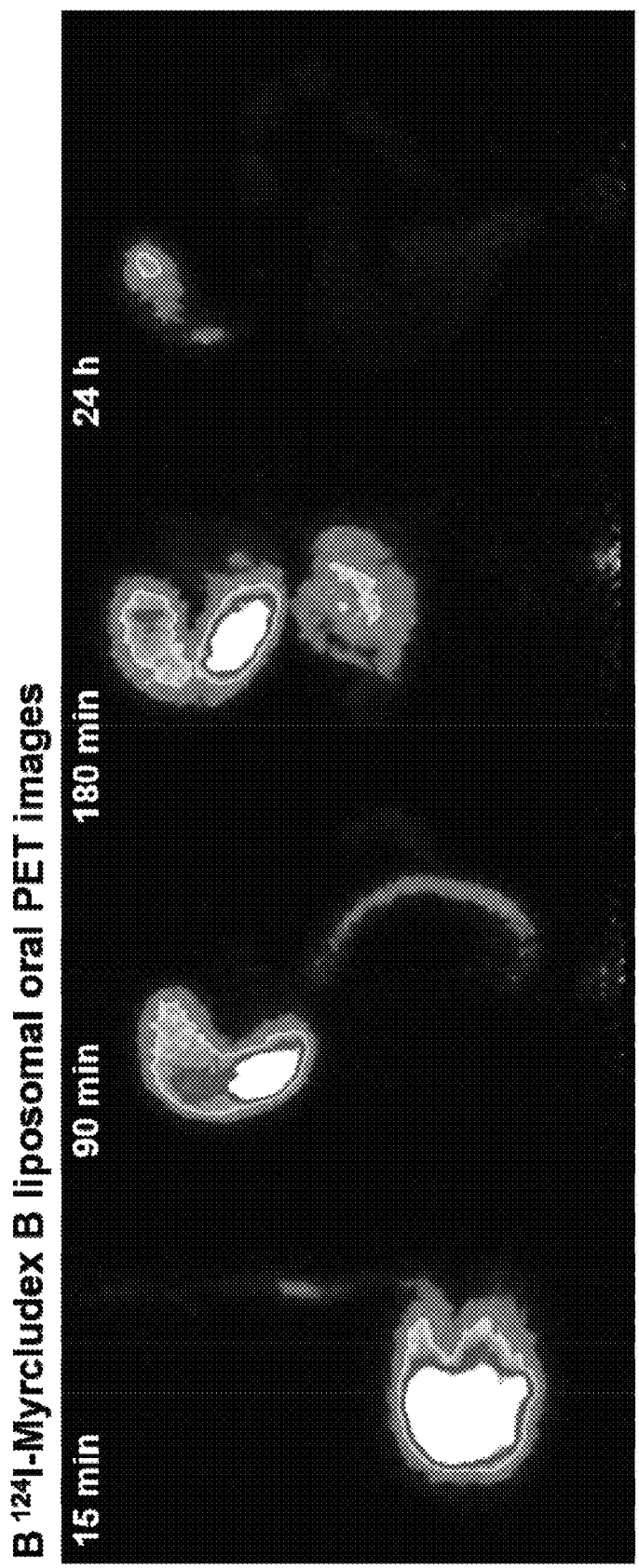
Figure 10:
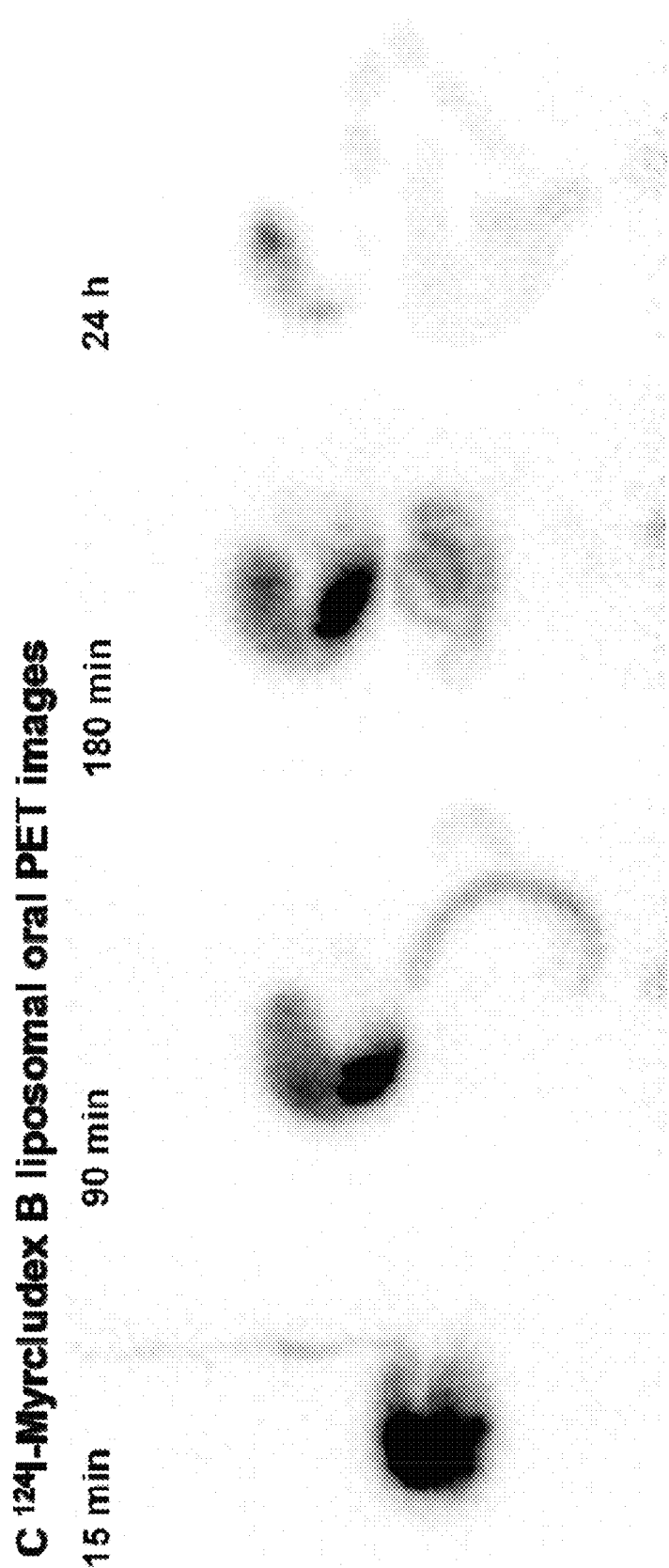

FIG. 10:
(A) PET-images of $^{68}$Ga labeled Myrcludex B (liposomal i.v.) 0-2 h post administration. (B) and (C) PET images of $^{124}$I labeled Myrcludex B (liposomal oral) 0-24 h post administration.

Figure 11:
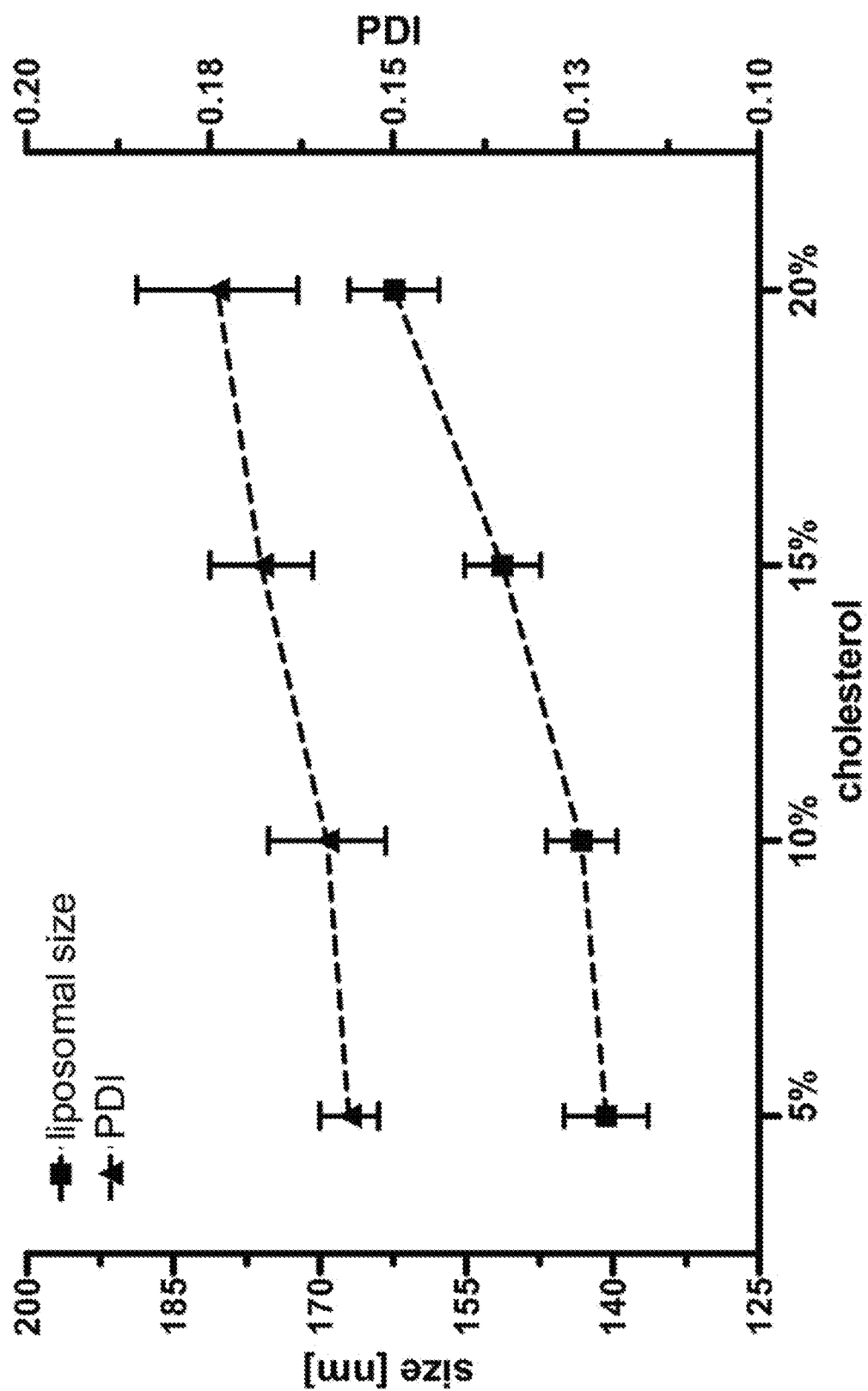

FIG. 11:
Plot of liposomal size and PDI versus various ratios of cholesterol (means±SD; n≥3).

Figure 12:
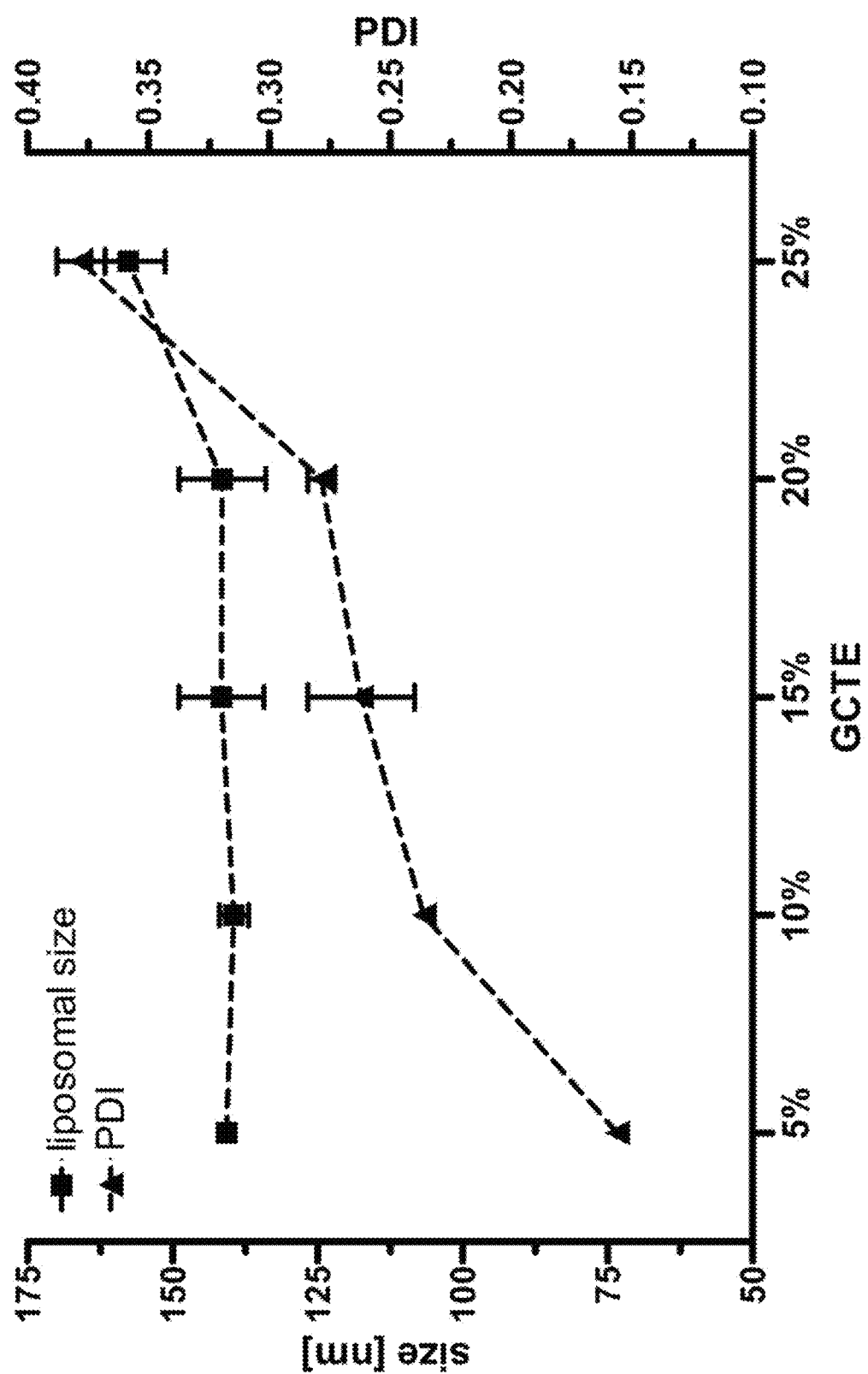

FIG. 12:
Plot of liposomal size and PDI versus various ratios of GCTE (means±SD; n≥3).

Figure 13:
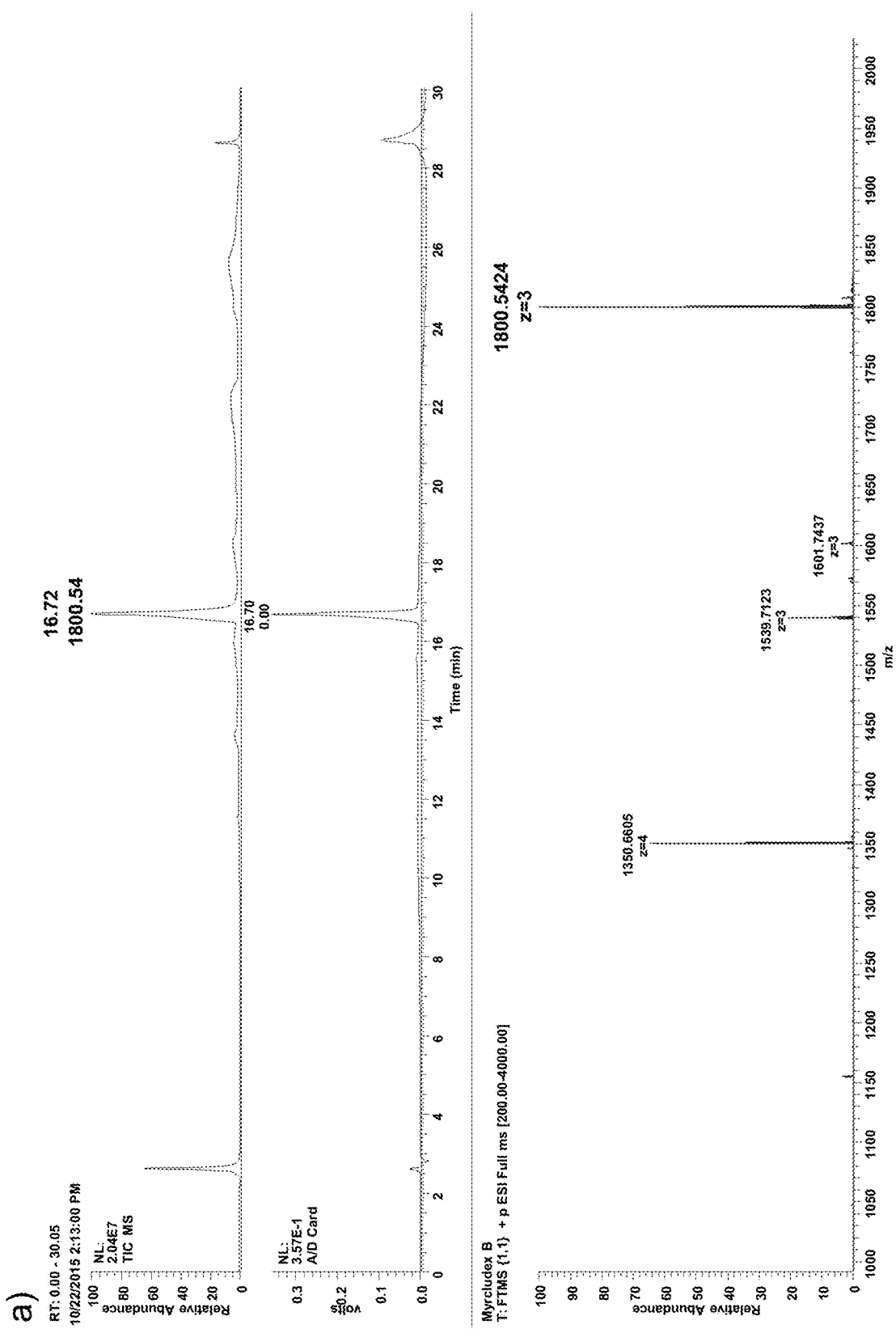
Figure 13:
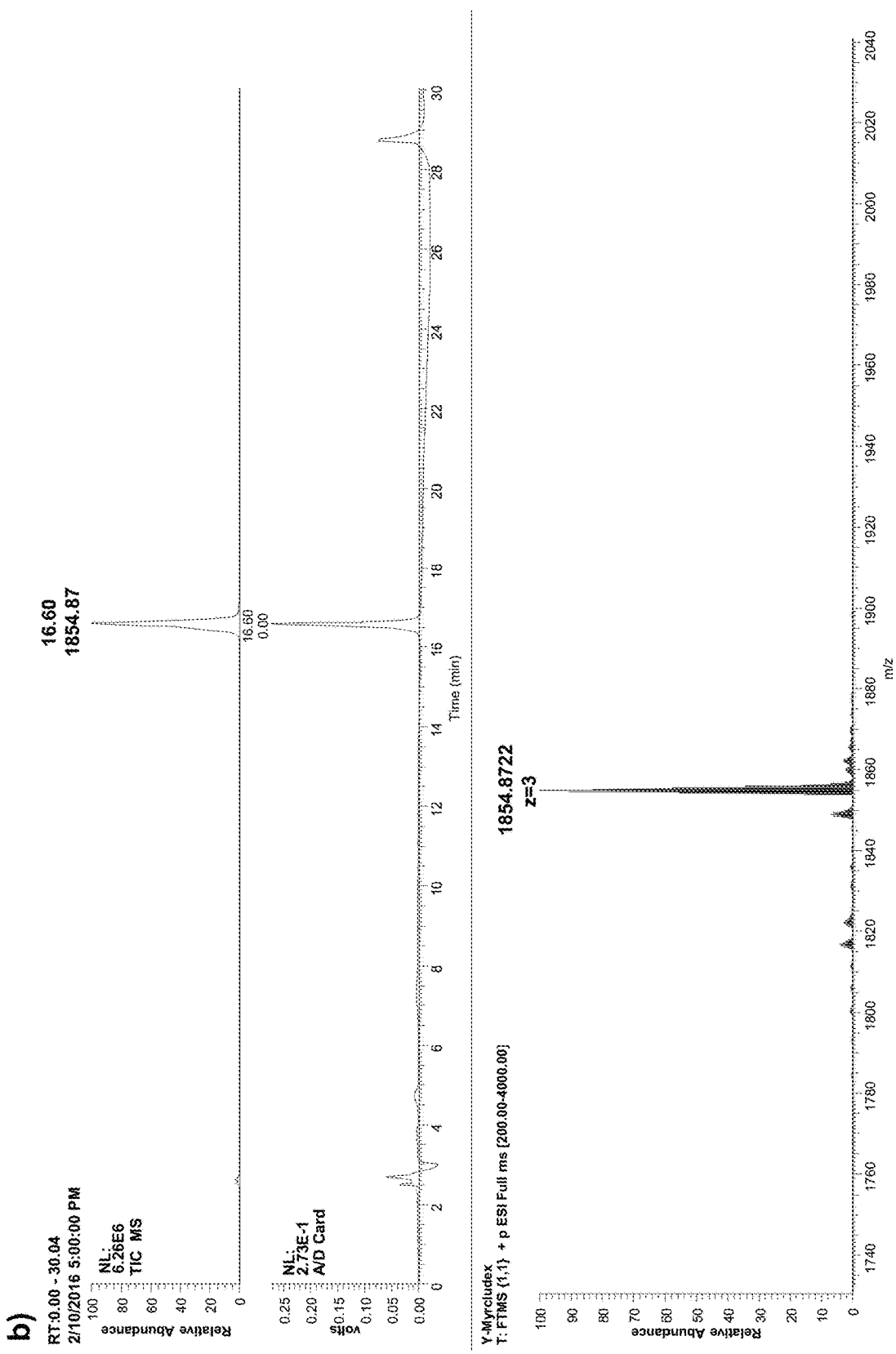

FIG. 13:
LC/MS-analysis of a) Myrcludex B and b) the tyrosine modified derivative.

Figure 14:
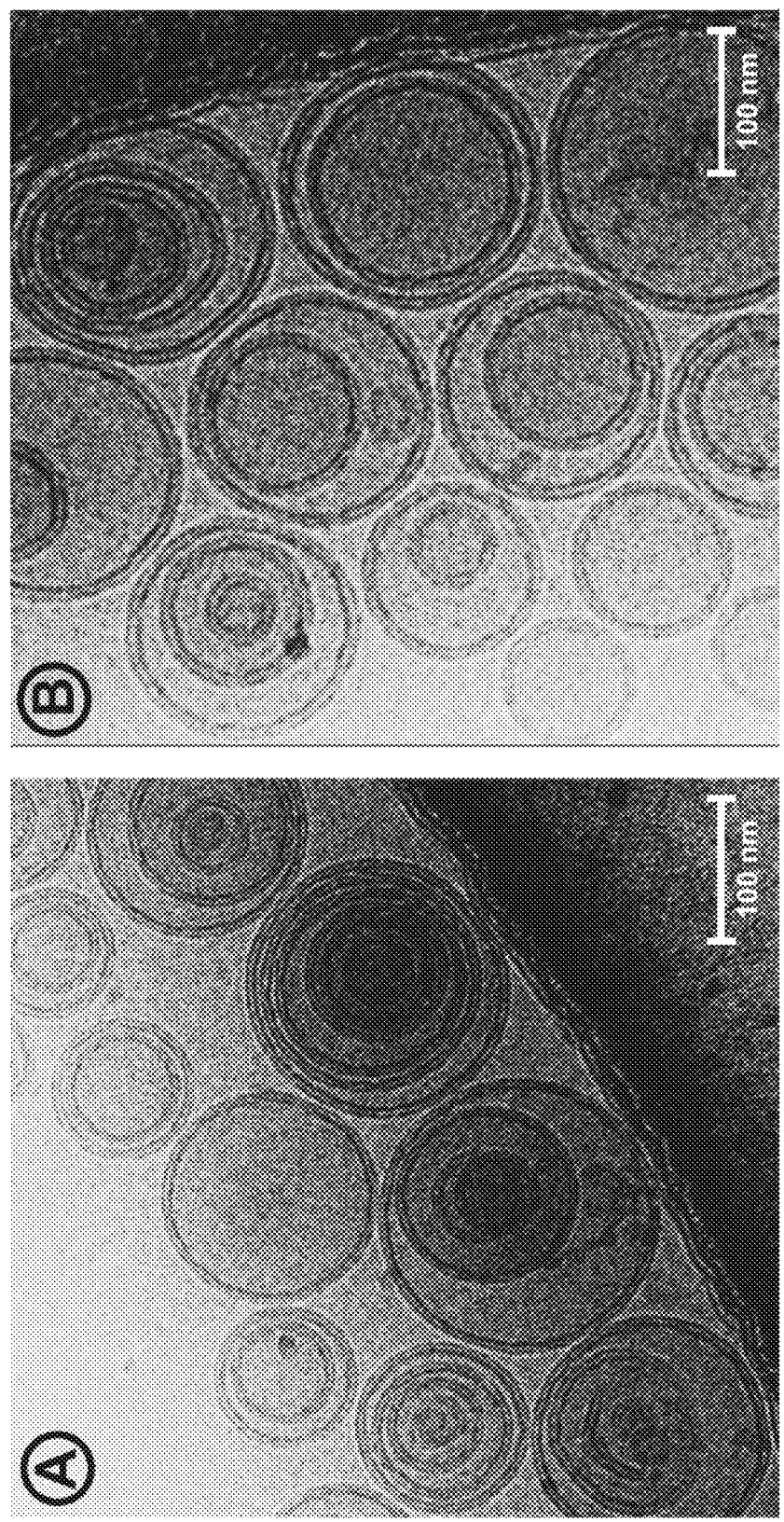

FIG. 14:
Cryo-electron micrographs showing the lamellar structure of (a) Myrcludex B standard-liposomes and (b) Myrcludex B GCTE-liposomes. The micrographs show both mono-lamellar and oligo-lamellar liposomes. Comparing both formulations, no difference in liposomal lamellarity could be observed.

Figure 15:
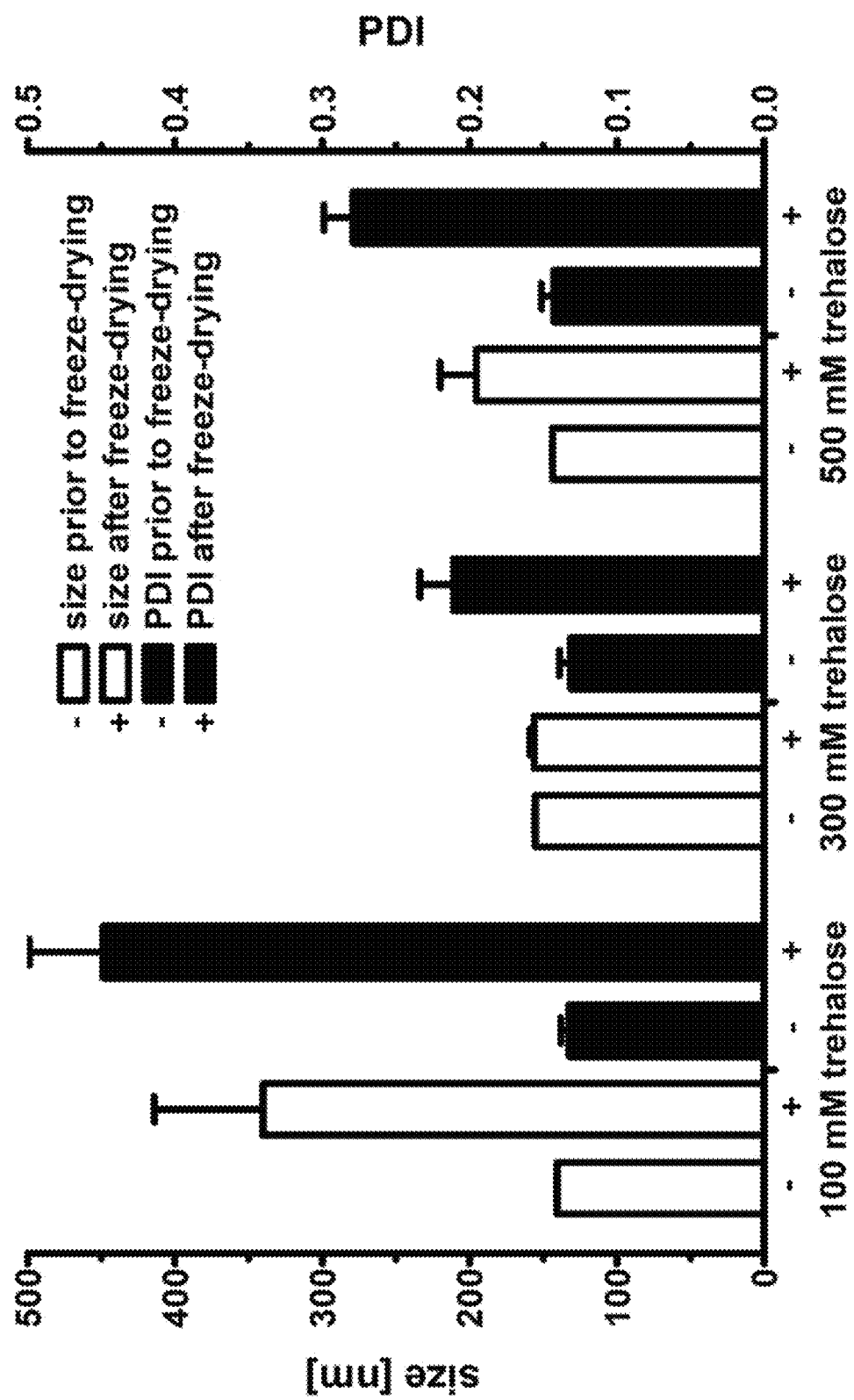

FIG. 15:
Comparison of liposomal size and PDI prior to/after freeze-drying using trehalose as lyoprotector at various molar ratios (means±SD; n≥3).

Figure 16:
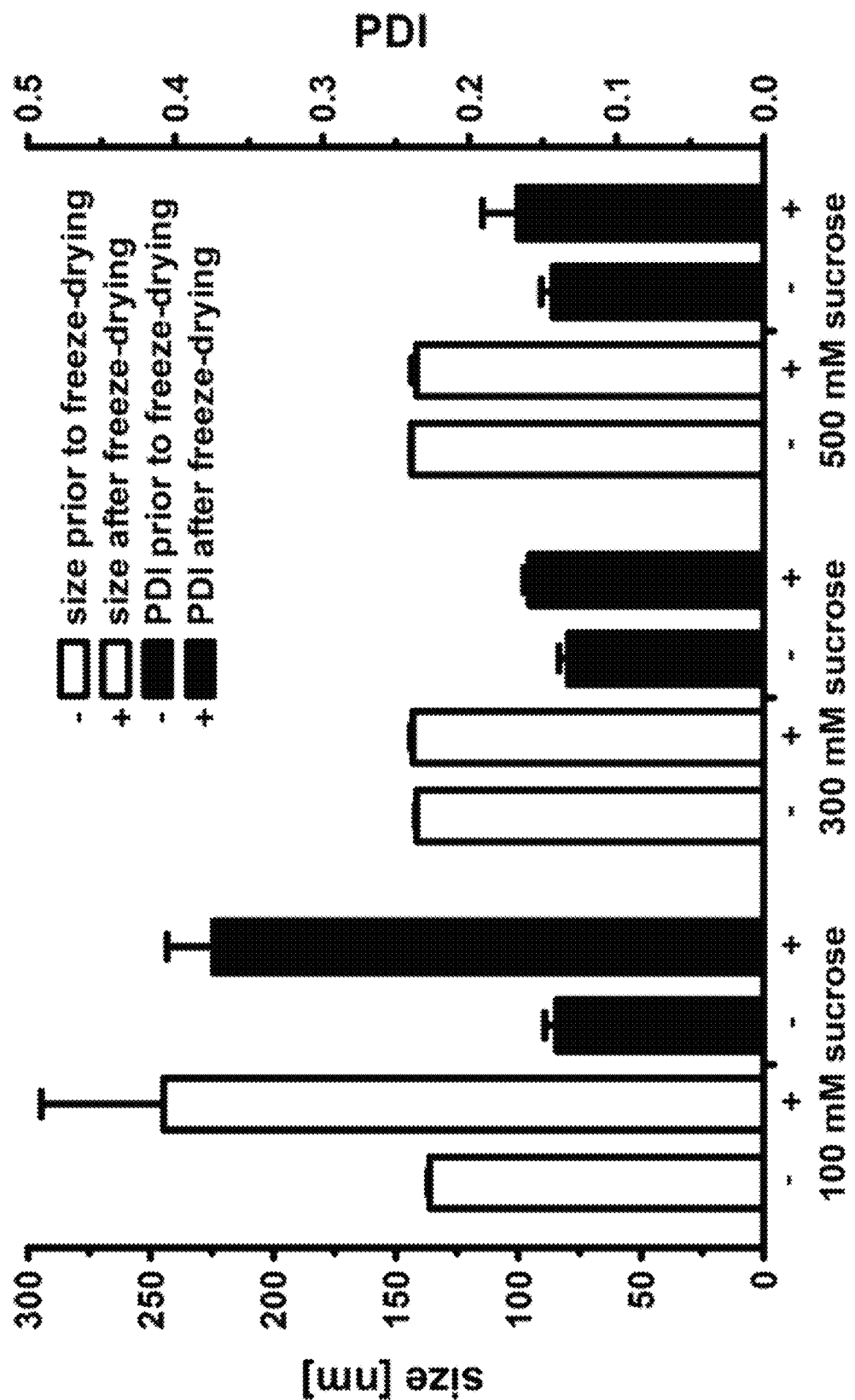

FIG. 16:
Comparison of liposomal size/PDI prior to/after freeze-drying using sucrose as lyoprotector for GCTE-liposomes at various ratios (means±SD; n≥5). Concentrations≥300 mmol provided promising results.

Figure 17:
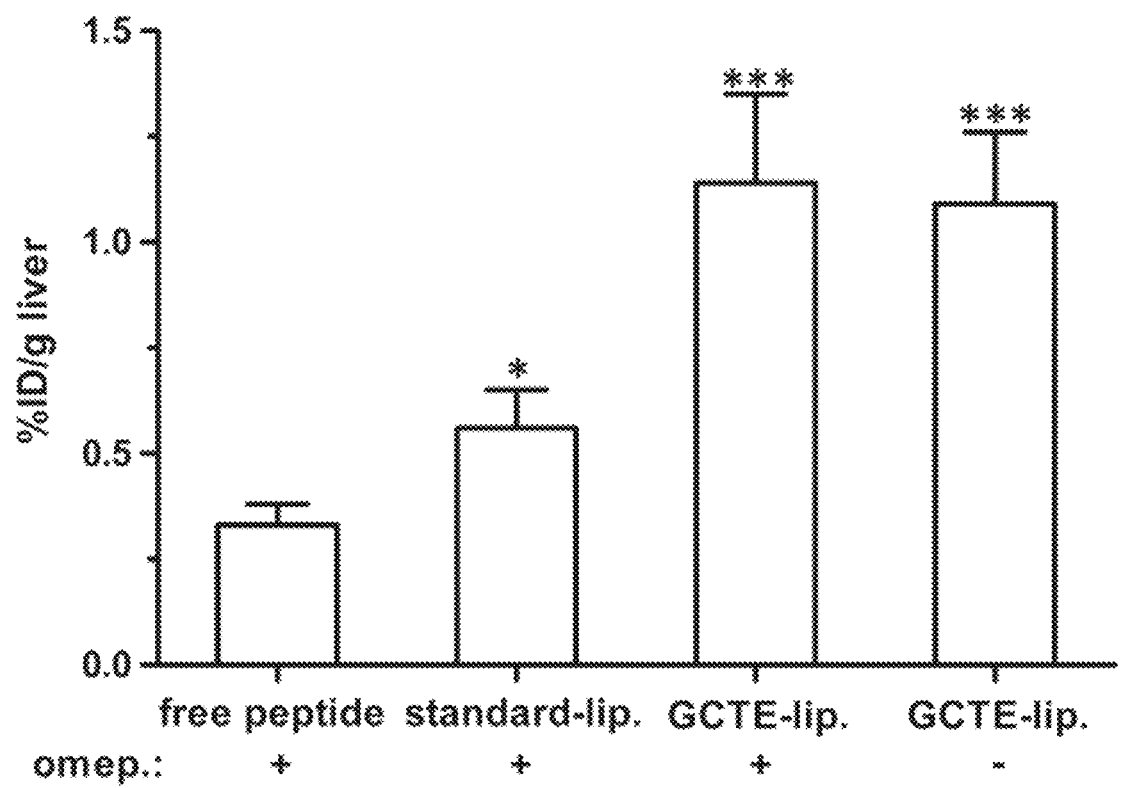

FIG. 17:
Uptake of Myrcludex B in liver tissue (means±SD; n=6) 3 h after oral administration. Both GCTE-liposomal formulations led to a significant increase in the uptake of Myrcludex B. In contrast, comparing the GCTE-liposomal groups, pretreatment with omeprazole (omep.) showed no significant difference in the uptake of Myrcludex B. Control (free peptide) and treatment groups were compared by the one-way ANOVA test and considered significant at *$p<0.05$, $p<0.01$ and *$p<0.001$.

Figure 18:
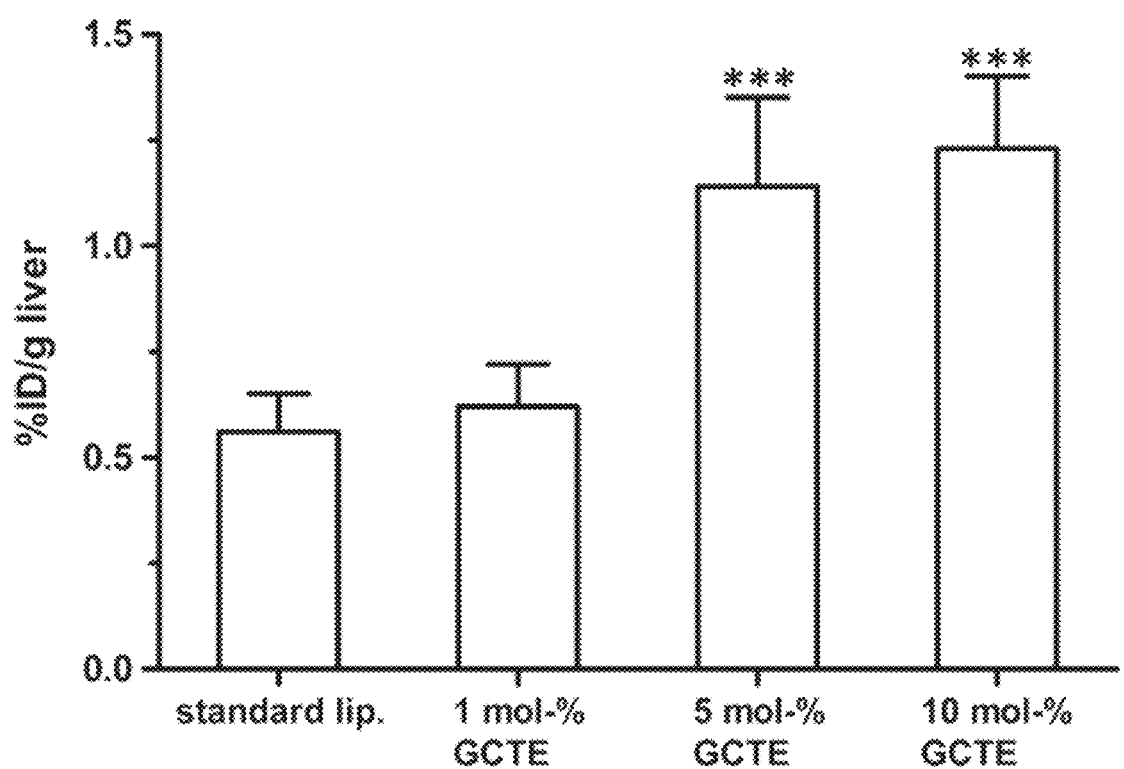

FIG. 18:
Uptake of Myrcludex B in liver tissue (means±SD; n=3) 3 h after oral administration using various GCTE concentrations. In contrast to the 1 mol-% GCTE-liposomal formulation, the other two formulations (5 mol-% and 10 mol-%) showed a significant increase in the uptake of Myrcludex B compared with the standard liposomes. Control (standard liposomes) and treatment groups were compared by the one-way ANOVA test and considered significant at *$p<0.05$, $p<0.01$ and *$p<0.001$.

Figure 19:
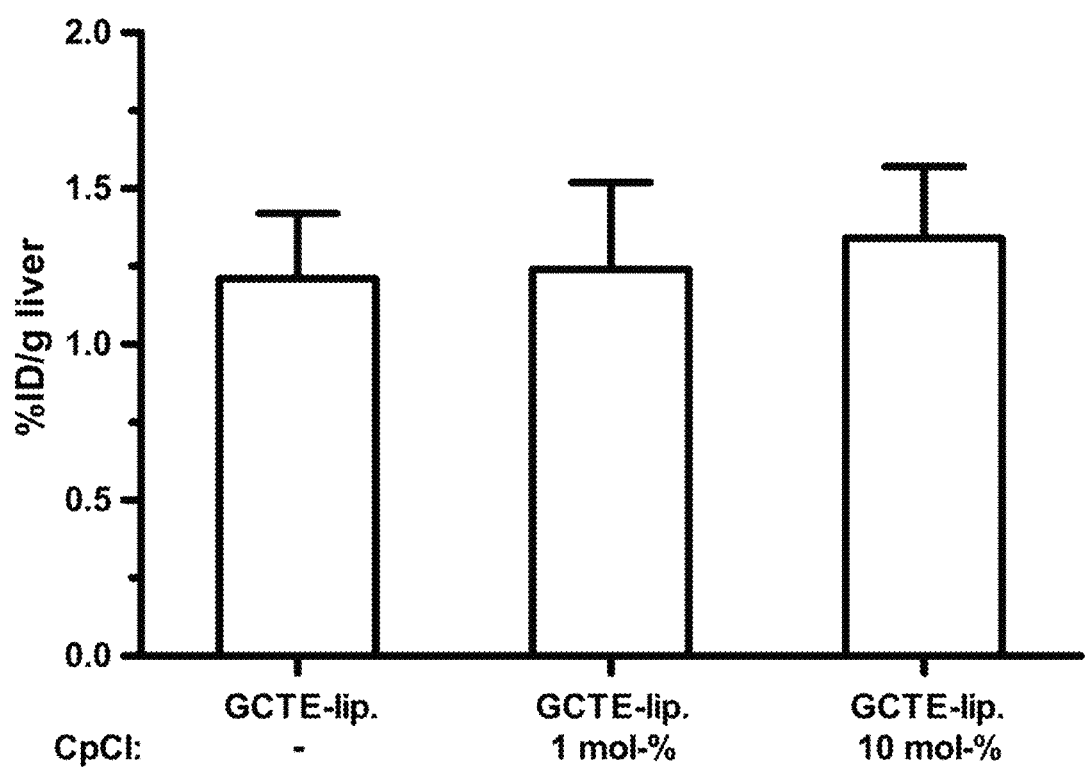

FIG. 19:
Comparison of the enrichment of Myrcludex B in the liver 3 h after oral administration of GCTE-liposomes and GCTE-liposomes containing additionally 1 mol-% and 10 mol-% of the bioenhancer cetylpyridinium chloride (means±SD; n=3).

Figure 20:
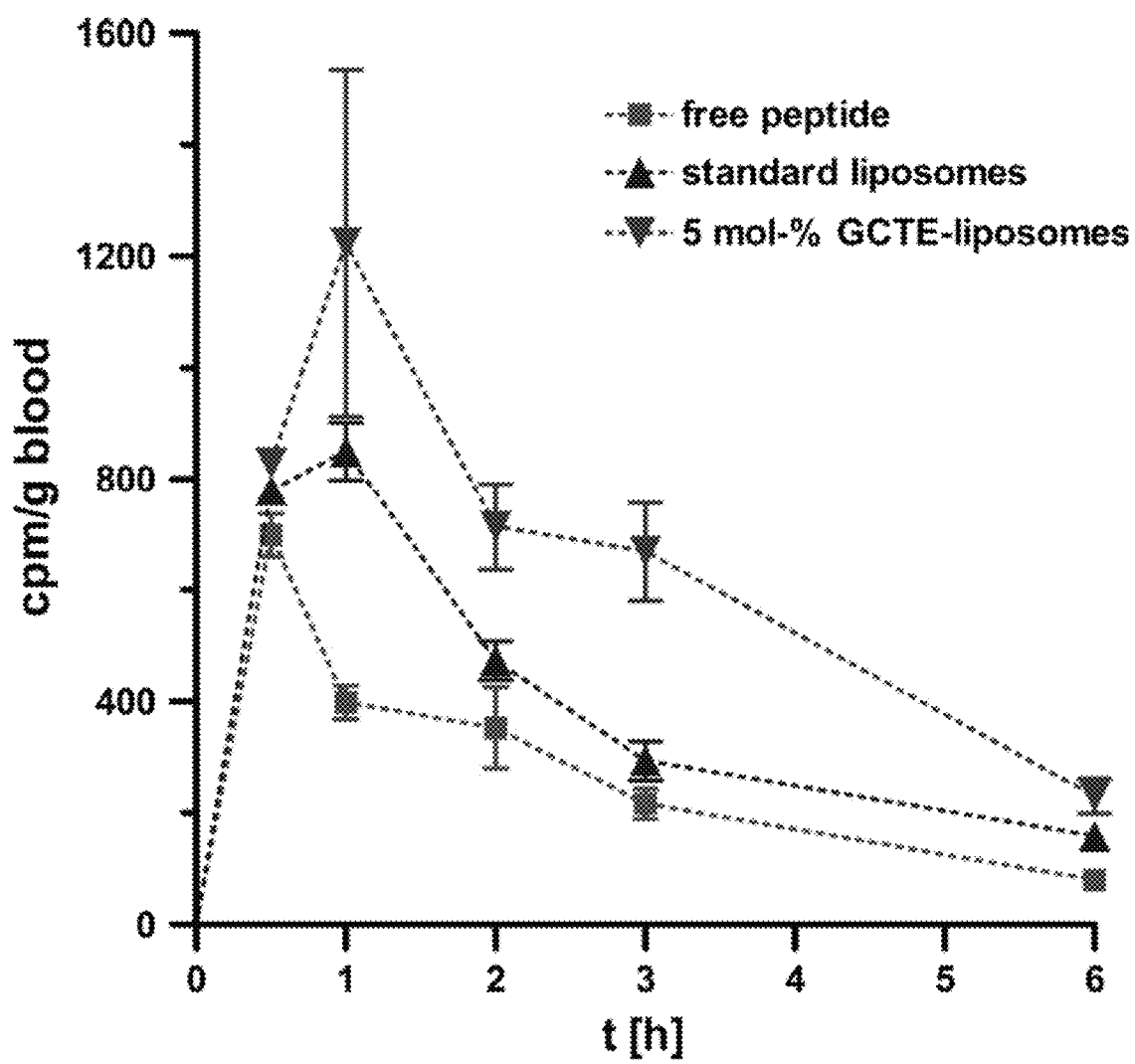

FIG. 20:
Quantification of radiolabeled Myrcludex B in blood samples. Concentration of the free peptide and the peptide incorporated in standard- and GCTE-liposomes (means±SD; n=3) 0-6 h after oral administration.

The present invention will be further illustrated by the following examples without being limited thereto.

EXAMPLES

Material and Methods:

Materials.

Lecithin (EPC) was obtained from AppliChem GmbH (Darmstadt, Germany); tetraether lipids were isolated from *S. acidocaldarius* (DSM No. 639; ATCC No. 33909) as known in the art; glass beads (0.75-1.0 mm) were purchased from Carl Roth GmbH & Co. KG (Karlsruhe, Germany);

NAP™-5 columns were obtained from GE Healthcare (Buckinghamshire, UK); Antra MUPS® (omeprazole) was purchased from Astra Zeneca GmbH (Wedel, Germany); silica gel 60 (0.063-0.200 mm) was obtained from Merck (Darmstadt, Germany); radioiodine was obtained from Perkin Elmer® (Boston, USA), Triton™ X-100, cholesterol and all solvents were purchased from Sigma Aldrich (Taufkirchen, Germany).

Isolation and Purification of GCTE and DGTE.

Cell growth and lipid extraction were performed as known in the art. S. acidocaldarius was separated from the medium and lyophilized using a Delta 1-20 KD from Martin Christ (Osterode, Germany). Lipids were isolated by Soxhlet extraction with chloroform/methanol (2:1 v/v) as known in the art. The extracted solvent was removed by rotary evaporation. Afterwards, the lipid mixture was dissolved in a mixture of chloroform, methanol and hydrochloric acid (8:3:1 v/v). The mixture was heated for 3 days at 60° C. to cleave the lipid head groups.

Finally, the lipids were extracted with chloroform/methanol (2:1) from the water phase. GCTE was separated by silica gel column chromatography with water/methanol (1:1 v/v) as first eluent (for prewashing the column), followed by water/methanol/chloroform (1:2.5:1 v/v) to remove unwanted lipids, and methanol/chloroform (1:1 v/v) to obtain the GCTE fraction.

Peptide Synthesis and Radiolabeling—Synthesis of Myrcludex B and Tyrosine-Modified Myrcludex B.

Both peptides were manufactured by solid-phase synthesis using the fluorenylmethoxycarbonyl/tert-butyl (Fmoc/tBu) chemistry on an Applied Biosystems 433A peptide synthesizer as known in the art. The tyrosine analogue (the tyrosine is located at the C-terminus of the peptide) was produced for radiolabeling by iodination for animal trials as described below, while for all other trials, Myrcludex B was used.

Peptide Synthesis and Radiolabeling—Radiolabeling of Tyrosine-Modified Myrcludex B.

For radiolabeling of the tyrosine-modified Myrcludex B, a 1 mM stock solution in water/dimethyl sulfoxide (DMSO) was prepared. The required amount of radioactive iodine-131 ($^{131}$I) was added to a 1:1 mixture of 25 µl of the stock solution and 25 µl of a 0.25 M pH 7.5 phosphate buffer. Labeling was performed using the chloramine T method known in the art. The reaction mixture was purified by semi preparative HPLC as known in the art. Afterward, the purity of the radiolabeled compound was determined by radio-HPLC (Agilent 1100 series) using a Chromolith® Performance RP-18e, 100-3 mm column applying a linear gradient of 0.1% TFA in water (eluent A) to 0.1% TFA in acetonitrile (eluent B) within 5 min; flow rate 2 ml/min; UV absorbance λ=214 nm; γ-detection.

Lipid Analyses.

A $^1$H-NMR spectrum of TEL was acquired using an Avance II 400 system (Bruker BioSpin GmbH, Rheinstetten, Germany). An IR spectrum was acquired using a Nicolet Avatar 320 FT-IR spectrometer (Thermo Fisher Scientific GmbH, Dreieich, Germany). Mass spectrometry was performed with a TSQ 700 (Thermo Finnigan MAT, Bremen, Germany) system.

Liposomes—Lipid Composition of Liposomes.

For all experiments, two different liposomal formulations were examined. GCTE-containing liposomes (85 mol-% EPC, 10 mol-% cholesterol and 5 mol-% GCTE) were compared with standard liposomes (90 mol-% EPC, 10 mol-% cholesterol). The most promising GCTE-liposomal formulation with respect to size and PDI was determined by the preparation of liposomes using various amounts of EPC, cholesterol and GCTE (cf. Example 3, infra).

Liposome Preparation.

A lipid film composition containing 85 mol-% lecithin, 10 mol-% cholesterol and 5 mol-% GCTE was used. All lipids were dissolved in chloroform/methanol 9:1 (v/v). All liposomal formulations were prepared by the film method as known on the art using the DAC technology as known in the art, the latter using a SpeedMixer™ (DAC150FVZ Hauschild Engineering GmbH & Co. KG, Hamm, Germany). First of all, the lipids were dissolved in chloroform/methanol 9:1 (v/v) to obtain 100 mmol stock solutions while Myrcludex B was dissolved in chloroform/methanol 1:1 (v/v; 1 mmol stock). 25 µl of the Myrcludex B stock solution was added to the lipid mixture; afterwards, the solution was dried by liquid nitrogen. The resulting lipid film was dried for 1 h in a vacuum chamber. Afterwards 20 mg of glass beads were added. The liposomes were prepared by speed mixing in 3 steps at 3540 rpm in a dual asymmetric centrifuge using a special vial holder as known in the art. Three runs were performed and different amounts of PBS were added (cf. Table 1, below).

TABLE 1

Characteristic settings of the speed mixing process.

| | Rotation in the speedmixer [min] | Volume calculation | Added volume of PBS [µl] |
|---|---|---|---|
| Run 1 | 30 min | Overall lipid mass (mg) × 1.5 | 28.4 |
| Run 2 | 5 min | Overall lipid mass (mg) × 2.5 | 47.3 |
| Run 3 | 1 min | Total volume-1. volume-2. volume | 127.0 |

Liposomes—Encapsulation Efficiency.

The encapsulation efficiency of Myrcludex B was determined by reversed phase HPLC (Agilent 1100 Series) using a C18 column (Chromolith® Performance RP-18e, 100-3 mm) applying a linear gradient of 0.1% TFA in water (eluent A) to 0.1% TFA in acetonitrile (eluent B) within 5 min (flow rate 2 ml/min; UV absorbance λ=214 nm). After the speed mixing process, the liposomes were divided into two parts with 100 µl each. Part 1 was used to calculate the 100% value obtained by destroying the liposomes by the addition of 50 µl 1% Triton™ X-100 and determining the area under the curve (AUC) of Myrcludex B by HPLC. Part 2 was purified by Sephadex G-25 gel filtration chromatography (NAP™-5 columns) and quantified as part 1. In order to determine the potential loss of lipids on the NAP™-5 columns during the purification of part 2, the concentration of cholesterol in the liposomal suspension was measured directly after the speedmixing process and after the purification using NAP™-5 columns. For both measurements, the liposomes were dissolved 1:10 (v/v) in methanol. Cholesterol was quantified by HPLC applying an isocratic gradient of acetonitrile/methanol (80:20 v/v) within 15 min (flow rate 2 ml/min; UV absorbance λ=208 nm) on a RP-18 column. The concentration of cholesterol before and after the purification step was compared and the correction factor C was determined in order to include the loss of lipids on the NAP™-5 columns into the calculation of the encapsulation efficiency. The encapsulation efficiency E (%) was calculated using the following equation:

$$E(\%)=([AUC] \text{ Myrcludex } B \text{ part } 2/[AUC] \text{ Myrcludex } B \text{ part } 1) \times 100\% \times C$$

whereby [AUC] Myrcludex B part 2 is the concentration of Myrcludex B in the purified liposomal fraction and [AUC] Myrcludex B part 1 is the concentration of Myrcludex B in the liposomal suspension. C is the correction factor considering the loss of lipids on the NAP™-5 columns.

Liposome Analyses—Particle Characterization; Particle Size, Polydispersity Index (PDI) and Zeta Potential.

The particle size and PDI of the liposomes was determined using a Zetasizer Nano ZS from Malvern™, while the encapsulation efficiency of Myrcludex B was determined by HPLC.

More specifically, the particle size, PDI and zeta potential of all liposomal formulations were determined at room temperature using a Zetasizer Nano ZS from Malvern™ (Malvern Instruments Ltd., Worcestershire, United Kingdom). Size and PDI were measured after dilution to a lipid concentration of 0.076 mg/ml with a 10 mM phosphate buffer with a pH of 7.4 using the automatic mode. The zeta potential was determined after dilution to a lipid concentration of 0.95 mg/ml by a 50 mM phosphate buffer with a pH of 7.4. The default settings of the automatic mode of the Zetasizer Nano ZS from Malvern™ (Malvern Instruments Ltd., Worcestershire, United Kingdom) were the following: number of measurements=3; run duration=10 s; number of runs=10; equilibration time=60 s; refractive index solvent 1.330; refractive index polystyrene cuvette 1.590; viscosity=0.8872 mPa s; temperature=25° C.; dielectric constant=78.5 F/m; backscattering mode (173°); automatic voltage selection; Smoluchowski equation.

Liposome Analyses—Particle Characterization; Cryo-EM Micrographs.

In order to determine the lamellar structure of the GCTE-liposomal formulation, samples were diluted to a concentration of 10 mg lipid per ml. Quantifoil grids (2/2) were glow discharged for 10 s in a $H_2$ and $O_2$ gas mixture. 3 µl of samples was applied to the grid and blotted at 4° C. and 100% humidity for 8-10 s in a FEI Vitrobot™. The grids were observed in a Krios™ microscope operated at 200 kV and liquid nitrogen temperature. The micrographs of the GCTE-liposomal sample were taken at 64,000× magnification as known in the art.

Freeze Drying of Liposomes—Long Term Storage Stability; Freeze-Drying Using Sucrose and Trehalose at Different Molar Ratios.

All liposomal formulations were freeze dried in a Delta 1-20 KD from Christ. The main drying was carried out at −20° C. for two days with a following secondary drying at 0° C. for at least six hours. Best results were obtained by the use of 300-500 mM sucrose as lyoprotector (FIG. 4 A, B).

More specifically, the main drying was carried out at −20° C. for 2 days followed by a secondary drying at 0° C. for at least 6 h. Sucrose or trehalose were used as lyoprotectors in a range of 100-500 mM as known in the art. Briefly, the liposomes were prepared as described above and the required amount of sucrose/trehalose was added. The liposomal suspension was partitioned into 50 µl aliquots and freeze-dried. In order to assess the quality of the freeze-dried products, the liposomes were rehydrated with 50 µl PBS and the size and PDI were determined.

Freeze Drying of Liposomes—Long Term Storage Stability; Recovery Rate of Myrcludex B after Freeze-Drying and Determination of Residual Moisture.

To determine the recovery rate of intact Myrcludex B after the freeze-drying process, a sample of the rehydrated liposomes was purified by Sephadex G-25 column chromatography (NAP™-5 columns) and 1:1 diluted with 1% Triton™ X-100. Myrcludex B was detected by HPLC using a C18 column (Chromolith® Performance RP-18e, 100-3 mm) and compared with the unpurified rehydrated product (calculation analogous to Liposomes—Encapsulation efficiency, supra). The residual moisture was determined by a moisture meter (Kern & Sohn GmbH, Balingen, Germany) using 100 mg of the freeze-dried liposomes by heating up to 120° C. in 90 s.

Animal Studies—Proof of Concept Study; Liver Accumulation of Myrcludex B Using Different Formulations.

The animal study was performed according to local authorities using male Wistar rats with a body weight of about 250-270 g. In the proof of concept study, a tyrosine-modified analogue of the lipopeptide Myrcludex B was labeled with $^{131}I$ and incorporated into the liposomes. The organ distribution 3 h after oral administration was measured by direct counting of liver tissue. In the first part of the study, four groups (n=6) of Wistar rats were formed. While three groups of rats (free peptide, standard liposomes and GCTE-liposomes) were pretreated with suspended Antra MUPS™ (omeprazole) by gavage (10 mg per rat) the day before the experiment, one group received GCTE-liposomes without omeprazole pretreatment in order to examine whether the pretreatment method will increase the oral availability of Myrcludex B. In the second part of the study, three groups of Wistar rats (n=3) were formed and received three different liposomal GCTE concentrations (cf. Table 2, below) in order to evaluate the best GCTE-liposomal composition for the oral uptake of Myrcludex B.

TABLE 2

Lipid composition of the three different GCTE-liposomal formulations

| | EPC (mol-%) | Cholesterol (mol-%) | GCTE (mol-%) |
|---|---|---|---|
| 1 mol-% GCTE-liposomes | 89 | 10 | 1 |
| 5 mol-% GCTE-liposomes | 85 | 10 | 5 |
| 10 mol-% GCTE-liposomes | 80 | 10 | 10 |

The rats were kept without food for 12 h before the experiment but with free access to water. Oral application took place by gavage. In the first part of the study, each rat of group 1 obtained a dose corresponding to 0.5 Mega Becquerel (MBq) of the labeled free peptide (negative control), while each rat of group 2 obtained a dose corresponding to 0.5 MBq of the standard liposomes and each rat of groups 3 and 4 obtained a dose corresponding to 0.5 MBq of the GCTE-liposomes. In the second part of the study, each rat of group 1 obtained a dose corresponding to 0.5 Mega Becquerel (MBq) of the 1 mol-% GCTE-liposomes while each rat of group 2 obtained a dose corresponding to 0.5 MBq of the 5 mol-% GCTE-liposomes and each rat of group 3 obtained a dose corresponding to 0.5 MBq of the 10 mol-% GCTE-liposomes. The rats were sacrificed after 3 h, the liver tissue was removed and weighed and the radioactivity was measured using a Berthold LB 951 G counter in comparison with standards. The liver-associated activity was related to the total injected dose (ID) and expressed as a percentage of the total injected dose per gram of tissue (% ID/g).

Animal Studies—Proof of Concept Study; Pharmakokinetic Study.

For the pharmacokinetic study, 3 groups of Wistar rats (n=3) were treated as described above and blood samples were taken at 0.5, 1, 2, 3 and 6 h post administration. The amount of the radioactivity of the blood samples was measured using a Berthold LB 951 G counter.

Animal Studies—Proof of Concept Study; Statistical Analyses.

Statistical data were processed using the Prism® software (GraphPad Software, San Diego, Calif., USA) and presented as mean±standard deviation of the mean (S.D.). Control and treatment groups were compared by one-way ANOVA test using the Prism® software and considered significant at *$p<0.05$, $p<0.01$ and *$p<0.001$.

Example 1

Pharmacokinetic Study

Myrcludex B has been labeled with $^{125}I$ and $^{131}I$ respectively in order to follow its organ distribution after oral administration (pharmacokinetic and biodistribution study) by direct counting of organ homogenates and blood samples.

The size of these liposomes (determined by dynamic light scattering in a Malvern Zetasizer) was in the range of 150 to 170 nm. The use of more than 10 mol-% TEL lead to both, an increase in the particle size distribution and also to a decrease in the incorporation rate.

In a first proof of concept study, the liposomes were administered to rats by gavage. Thereby, the tyrosin-modified lipopeptide Myrcludex B was labeled with $^{131}I$ in order to detect the peptide, and incorporated into the liposomes. The animals received either the free peptide or TEL-containing (5 mol-% TELs) liposomes. In comparison to the control group (free peptide), the blood levels of the liposomal group showed a threefold higher count rate indicating a much higher Myrcludex B uptake of the TEL-liposomal group (FIG. 5).

Example 2

Labeled Myrcludex B and liposomes containing the same were prepared as in Example 1.

For the biodistribution study, three groups of Wistar rats (three rats per group) were formed. The rats were kept without food for 12 h but with free access to water. One day before the experiment, the rats were pretreated with suspended Antra MUPS (omeprazole) by gavage. Oral application took place by gavage. Each rat of group 1 got 500 μl of the labeled free peptide, while each rat of group 2 got 500 μl of the standard liposomal preparation and each rat of group 3 got 500 μl of the TEL-liposomal preparation.

The control group in which each rat received 500 μl of the labeled free peptide showed a liver uptake of Myrcludex B of only 0.33% initial dose (ID)/g compared with standards (FIG. 7). Group 2 (in which each rat received a conventional liposomal formulation consisting of 85% lecithin and 15% cholesterol) showed an increase in the liver uptake (0.56% ID/g) compared with standards (FIG. 8).

In comparison to the standard liposomes group, the group which received TEL-liposomes showed by far the highest liver uptake of Myrcludex B (1.14% ID/g) (FIG. 9). Due to the fact that in general the weight of the liver of Wistar rats is about 6 to 8 g, in total a liver uptake of about 8 to 10% of the initial dose of Myrcludex B could be detected.

FIG. 6 shows the comparison of the enrichment of Myrcludex B in liver tissue a) % ID/g and b) % ID 3 h after oral administration. The TEL-liposomal group showed the highest uptake of Myrcludex B (1.14% ID/g) compared 0.56% ID/g of the standard liposomal group and 0.33% ID/g of the group which got the free peptide.

For a new approach of biodistribution studies, the peptide Myrcludex B was combined with the chelating agent 1,4,7,10-tetraazacyclododecane-1,4,7,10-tetraacetic acid (DOTA). This combination allowed for an alternative labeling technique for Myrcludex B using $^{68}Ga$ as radionuclide. $^{68}Ga$ (half-live=68 min), as a positron-emitting agent, allowed the use of the modern molecular imaging method positron emission tomography (PET). Using PET, images of the biodistribution of the labeled peptide administered to rats, could be obtained (FIG. 10). In order to obtain PET images of orally administered liposomal Myrcludex B, the peptide was labeled by $^{124}I$. PET images of i.v. administered liposomal Myrcludex B were obtained by chelation with DOTA/$^{68}Ga$.

Example 3

Determination of Particle Size and PDI of Different Liposomal Formulations

In order to determine the best liposomal formulation with respect to size and PDI, liposomes were prepared using various amounts of the liposomal components EPC, cholesterol and GCTE. First, different amounts of cholesterol were mixed with the standard lipid EPC. The addition of more than 10 mol-% of cholesterol resulted in a moderate increase in liposomal size and PDI (FIG. 11).

In the second step, the concentration dependency of GCTE (0-25 mol-%) was examined using x mol-% EPC and 10 mol-% cholesterol as standard lipid mixture for each GCTE concentration. The amount of EPC was calculated by the following equation:

$$\text{Mol-\% EPC}=100\text{ mol-\%}-10\text{ mol-\% cholesterol}-x\text{ mol-\% GCTE}$$

with x mol-% GCTE=0-25

The results showed nearly constant values of the liposomal size. In contrast, a significant increase in the PDI could be observed (FIG. 12).

For fulfilling the requirement of small liposomal size accompanied by low PDI, a lipid mixture of 5 mol-% GCTE, 10 mol-% cholesterol and 85 mol-% EPC was considered to be the ideal liposomal formulation.

Example 4

Isolation of Tetraether Lipids

The isolation procedure yielded the purified tetraether lipids with only slight variations in the number of pentyl rings (3-5) in the lipophilic chains as determined by mass spectrometry and thin-layer chromatography in comparison with standards. The number of pentyl rings is influenced by the temperature during cultivation of the archaea. Approximately 1 g of tetraether lipids could be obtained per 400 g of wet cell mass.

Example 5

Peptide Synthesis and Radiolabeling

Synthesis of Myrcludex B and the Tyrosine-Modified Myrcludex B Derivative.

The lipopeptides could be obtained in high purity as determined by LC/MS on an Exactive mass spectrometer (Thermo Scientific).

Myrcludex B and the tyrosine modified derivative were analyzed by mass spectrometry. The mass spectrum of Myrcludex B shows a main signal at $$\frac{m}{z} = 1800.64\ (z = 3)$$

which corresponds to the peak of Myrcludex B (molecular weight=5399 g/mol) while the mass spectrum of the derivative shows a main signal at $$\frac{m}{z} = 1854.87\ (z = 3)$$

which corresponds to its molecular weight of 5562 g/mol (FIG. 13).

Radiolabeling of the Tyrosine-Modified Myrcludex B.

The $^{131}$I-radiolabeling of the tyrosine modified Myrcludex B yielded the desired product in high purity (>95%) as determined by radio-HPLC. The labeling efficiency using the chloramine T method was 65% of the radioactivity applied.

Example 6

Encapsulation Efficiency

The recovery of lipids after purification by the NAP™-5 columns was found to be 89.51±0.58%. This corresponds to a loss of lipids of 10.49±0.58%, resulting in a correction factor of lipid loss of C=1.12. The GCTE-liposomes containing Myrcludex B showed an encapsulation efficiency of 65.67±2.91% which is comparable with the determined value of the standard liposomes (63.10±2.02%). This emphasizes the high encapsulation efficiency of the DAC method compared with other common preparation methods, as previously shown for peptide drugs. An encapsulation efficiency of about 50% for 70 kDa FITC-Dextran using the speedmixing technology has been found, while, in contrast, other preparation methods for the incorporation of peptides into liposomes such as the film method followed by extrusion used for the encapsulation of octreotide only led to an encapsulation efficiency of 13.0% (m/m) [17].

Example 7

Particle Characterization
Particle Size, PDI and Zeta Potential.

The DAC-method applied yielded Myrcludex B GCTE-liposomes with high homogeneity in size, PDI and encapsulation efficiency (cf. Table 3, below). Compared with the standard liposomes, size and PDI of the GCTE-liposomes showed a moderate increase while nearly no difference in the zeta potential could be detected (−3.74±0.28 mV for standard liposomes and −4.20±0.48 mV for GCTE-liposomes). An increase in the amount of GCTE (up to 25 mol-%; for data see FIG. 12) led to an increase in the liposomal PDI, while, in contrast, the size remained nearly constant. The liposomes containing the bioenhancer CpCl (0-25 mol-%) showed constant values regarding the liposomal size (for data see Table 4, below) while the PDI increased when using 25 mol-% CpCl. This drastic increase might be traced back to differences in the phase transition temperature, as no agglomeration of liposomes could be observed.

|  | Size (nm) | PDI | Zeta potential (mV) |
| --- | --- | --- | --- |
| GCTE-liposomes | 140.7 ± 4.3 | 0.156 ± 0.010 | −4.20 ± 0.48 |
| Standard-liposomes | 131.3 ± 1.5 | 0.137 ± 0.022 | −3.74 ± 0.28 |

TABLE 4

Particle characterization of 1-25 mol-% CpCl/GCTE-liposomes (means ± SD; n ≥ 5)

|  | Size (nm) | PDI | Zeta potential (mV) |
| --- | --- | --- | --- |
| 1 mol-% CpCl/GCTE | 127.72 ± 2.13 | 0.164 ± 0.016 | 7.29 ± 0.61 |
| 10 mol-% CpCl/GCTE | 129.89 ± 5.34 | 0.204 ± 0.035 | 17.13 ± 0.74 |
| 25 mol-% CpCl/GCTE | 144.99 ± 10.06 | 0.494 ± 0.050 | 29.50 ± 1.47 |

Cryo-EM.

The cryo-electron micrographs (FIG. 14) show the lamellar structure of a diluted sample of the Myrcludex B standard- and the Myrcludex B GCTE-liposomes. A mixture of mono- and oligolamellar liposomes could be detected, while previously mostly multi-lamellar structures for GCTE-liposomes were found by using higher amounts of GCTE. Therefore, the lamellarity of GCTE-liposomes seems to be dependent on both the amount of GCTE and also the liposomal preparation technique.

Example 8

Long Term Storage Stability
Freeze-Drying Using Sucrose and Trehalose as Lyoprotectors at Different Molar Ratios.

The freeze-drying of liposomes containing sucrose and trehalose in different molar ratios as lyoprotectors resulted in a comparable size and PDI for certain molar ratios of sucrose when compared to the data measured prior to the freeze-drying process (FIG. 16). Regarding this liposomal formulation, the minimal concentration of sucrose should be at least 300 mM. These results are in accordance with previous findings that the best protecting effect for a liposomal formulation consisting of EPC and cholesterol uses at least 0.4 M sucrose. An increase in the concentration of the lyoprotector (shown for 500 mM sucrose) does not provide better results regarding size and PDI of the liposomes. Regarding both lyoprotectors, sucrose provided better results compared with trehalose (data see FIG. 15). For this reason, 300 mM sucrose was used for the following determination of the recovery rate of intact Myrcludex B and also for the measurement of the residual moisture after the lyophilization process.

Recovery Rate of Intact Myrcludex B after Freeze-Drying and Residual Moisture.

After the freeze-drying process the recovery rate of intact Myrcludex B incorporated in the GCTE-liposomes was 83.3±1.3%. The remaining Myrcludex B (14.8±1.6%) could be detected as the intact peptide. It was removed using a NAP-5™ column.

In order to ensure the long term stability of the lyophilized liposomes, low residual moisture has to be achieved. The residual moisture of the Myrcludex B liposomal formulation using sucrose (300 mM) as lyoprotector was 4.2±1.5%. These findings are in accordance with previous findings determining a residual moisture of 2-4% for liposomes consisting of EPC and cholesterol using sucrose and trehalose as lyoprotectors. In order to determinate the long term stability of the lyophilized product, samples were stored at −20° C. for 3 months. After resuspension, the size, PDI and recovery rate were measured. All values were comparable with the values determined directly after the freeze-drying process (Table 5).

TABLE 5

Comparison of the rehydrated GCTE-liposomes directly and 3 months after freezedrying (means ± SD; n P .3).

|  | Size (nm) | PDI | Recovery of Myrcludex B (%) |
|---|---|---|---|
| After freeze-drying | 145.9 ± 4.0 | 0.156 ± 0.017 | 83.3 ± 1.3 |
| After 3 months | 146.1 ± 3.7 | 0.163 ± 0.014 | 82.7 ± 1.6 |

Example 9

Proof of Concept Study: Animal Trials
Liver Accumulation of Myrcludex B Using Different Formulations.

The first part of the animal studies showed a significant increase in the enrichment of Myrcludex B in liver tissue (FIG. 17) using GCTE-liposomes (1.14% ID/g) when compared with standard liposomes (0.56% ID/g) and the labeled free peptide (0.33% ID/g). Considering an average liver weight of approximately 6-8 g in a 250 g Wistar rat, the results show that at least 7% of the initial dose of Myrcludex B had been absorbed. This highlights the strong increase in the oral availability of Myrcludex B by the use of GCTE-liposomes. Further, it was examined if pretreatment with omeprazole for the 5 mol-% GCTE-liposomal formulation would lead to an increase in the oral availability of Myrcludex B. However, there was no significant difference apparent between the pretreated and the not pretreated group (FIG. 17).

In the second part of the animal studies three different GCTE concentrations were compared. In contrast to the 5 mol-% and 10 mol-% GCTE-liposomal formulations, for the 1 mol-% GCTE-liposomal formulation no significant increase in the oral availability of Myrcludex B in comparison with the standard liposomes could be observed (FIG. 18). Furthermore, there was no significant difference between the 5 mol-% and the 10 mol-% GCTE-liposomal formulations. For this reason, 5 mol-% of GCTE seems to be sufficient for the stabilizing effect of the tetraether lipids.

The addition of the bioenhancer cetylpyridinium chloride (CpCl; 1-10 mol-%) to the GCTE-liposomal formulation didn't show a significant increase in the oral availability of Myrcludex B (FIG. 19).

In particular, it was tested if the addition of bioenhancers would lead to an increase in the oral availability of Myrcludex B. For this purpose, 1-25 mol-% of the bioenhancer cetylpyridinium chloride (CpCl) were added to the GCTE lipid mixture and the size, PDI and the zeta potential of the liposomes were determined. While the 1 mol-% and 10 mol-% CpCl/GCTE-liposomes showed comparable values regarding size and PDI, a high increase in the PDI of the 25 mol-% CpCl/GCTE-liposomes (cf. Table 4, supra) could be observed.

With respect to the high PDI of the 25 mol-% CpCl/GCTE liposomes, only the liver uptake of the 1 mol-% and 10 mol-% CpCl/GCTE-liposomes in male Wistar rats was determined and compared with the GCTE formulation. Regarding both formulations containing the bioenhancer CpCl, no significant increase in the oral availability of Myrcludex B could be observed (FIG. 19).

Pharmakokinetic Study.

The blood samples of the GCTE-liposomes group (AUC=3550) showed a significant increase in the uptake 0-6 h after oral administration compared to the standard liposomes (AUC=2175) and the labeled free peptide group (AUC=1705; FIG. 20).

The animal trials highlight the potential of the GCTE-formulation for the oral application of Myrcludex B. In particular, a 3.5-fold increase in the oral availability of Myrcludex B could be shown. Furthermore, using sucrose as lyoprotector, it could be shown that long term storage of the GCTE-liposomes by freeze-drying and rehydration can be enabled without destroying the incorporated peptide drug.

Besides the use of GCTE-liposomes, there exists a plentitude of other attempts to enhance the oral availability of macromolecular drugs. When compared with liposomes bearing surface modifications—recently the most common strategy for oral peptide delivery—e.g. coating of liposomes with thiolated chitosan or chitosan-aprotinin, the GCTE formulation shows the big advantage that no coupling step is required. This enables a faster and more reliable liposomal production.

CONCLUSION

In the present invention, an oral delivery system for the investigational hepatitis B drug Myrcludex B could be established by the use of GCTE-liposomes. The film method with subsequent dual asymmetric centrifugation enabled the fast and reproducible liposomal preparation. The GCTE-liposomes showed high homogeneity in size, PDI and encapsulation efficiency. The long term storage of the liposomes could be achieved by freeze-drying using sucrose as lyoprotector without destroying the incorporated peptide drug. Taken together, this study shows that the encapsulation of Myrcludex B into GCTE-liposomes led to a significant improvement in the oral uptake independent of pretreatment with omeprazole.

The invention claimed is:

1. A liposomal composition for oral administration comprising:
   (a) liposomes comprising
      glycerylcaldityltetraether (GCTE) in an amount of 4 to 6 mol-% based on the total lipid amount,
      egg phosphatidylcholine (E-PC; lecithin) in an amount of 80 to 90 mol-% based on the total lipid amount, and
      cholesterol in an amount of 5 to 15 mol-% based on the total lipid amount,
      wherein said liposomes exhibit a Z-Average measured by dynamic light scattering after dilution in aqueous medium of 100 to 250 nm and a polydispersity index (PDI) of at most 0.2, and
   (b) the lipopeptide Myr-HBVpreS/2-48 as part of said liposomes.

2. The liposomal composition for oral administration according to claim 1 for use in the prevention and/or treatment of a viral hepatitis.

\* \* \* \* \*